United States Patent
Daya et al.

(10) Patent No.: US 12,077,782 B2
(45) Date of Patent: Sep. 3, 2024

(54) VIRAL CLEARANCE BY LOW pH HOLD

(71) Applicant: Regeneron Pharmaceuticals, Inc., Tarrytown, NY (US)

(72) Inventors: Jena Daya, Brandon, VT (US); Valerie Ann Cusick, Whitehouse Station, NJ (US); John Mattila, Nyack, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 288 days.

(21) Appl. No.: 17/317,602

(22) Filed: May 11, 2021

(65) Prior Publication Data
US 2021/0348131 A1    Nov. 11, 2021

Related U.S. Application Data

(60) Provisional application No. 63/023,154, filed on May 11, 2020.

(51) Int. Cl.
*C12N 7/00* (2006.01)
*C07K 1/14* (2006.01)
*C07K 16/10* (2006.01)

(52) U.S. Cl.
CPC .......... *C12N 7/00* (2013.01); *C07K 1/14* (2013.01); *C07K 16/1036* (2013.01); *C12N 2740/13063* (2013.01)

(58) Field of Classification Search
None
See application file for complete search history.

(56) References Cited

PUBLICATIONS

Brorson K, Krejci S, Lee K, Hamilton E, Stein K, Xu Y. Bracketed generic inactivation of rodent retroviruses by low pH treatment for monoclonal antibodies and recombinant proteins. Biotechnol Bioeng. May 5, 2003;82(3):321-9. doi: 10.1002/bit. 10574. PMID: 12599259. (Year: 2003).*

Chinniah S, Hinckley P, Connell-Crowley L. Characterization of operating parameters for XMuLV inactivation by low pH treatment. Biotechnol Prog. Jan.-Feb. 2016;32(1):89-97. doi: 10.1002/btpr. 2183. Epub Nov. 5, 2015. PMID: 26488618. (Year: 2015).*

Buss NA, Henderson SJ, McFarlane M, Shenton JM, de Haan L. Monoclonal antibody therapeutics: history and future. Curr Opin Pharmacol. Oct. 2012;12(5):615-22. doi: 10.1016/j.coph.2012.08. 001. Epub Aug. 21, 2012. PMID: 22920732. (Year: 2012).*

Brorson Kurt et al: "Bracketed generic inactivation of rodent retroviruses by low pH treatment for monoclonal antibodies and recombinant proteins", Biotechnology and Bioengineering, Wiley,US, vol. 82, No. 3, May 5, 2003 (May 5, 2003), pp. 321-329.

Li J J et al: "Monoclonal Antibody Aggregate Polishand Viral Clearance Using HydrophobicInteraction Chromatography", Thermofisher Scientific, vol. 17, No. 11-12, Nov. 1, 2019 (Nov. 1, 2019), pp. 1-7, XP002802707, the whole document, p. 4-p. 5.

Anonymous: "Viral Safety—Practical Solutions for Risk Control", Jun. 1, 2018 (Jun. 1, 2018), pp. 1-39, XP055713559, Retrieved from the Internet: URL:https://www.pall.com/content/dam/pall/biopharm/lit-library/gated/special/19-07511-USD3364-Virus-Safety-Practical-Solutions-Risk-Control-BOOK-EN.PDF [retrieved on Jul. 10, 2020].

International Search Report and Written Opinion of PCT/US2021/031825, International Filing Date May 11, 2021, Date of Mailing Aug. 26, 2021.

Gail Sofer et al., "Part 6. Inactivation Methods Grouped by Virus", BioPharm International, Apr. 1, 2003, XP055481662 (6 pages).

Kyeongjin Seo et al., "Effect of Temperature, pH, and NaCl on the Inactivation Kinetics of Murine Norovirus", Journal of Food Protection, vol. 75, No. 3, Mar. 1, 2012 (Mar. 1, 2012), XP093145785, <https://dul.usage.elsevier.com/doi/>, pp. 533-540.

\* cited by examiner

*Primary Examiner* — Benjamin P Blumel
*Assistant Examiner* — Jeffrey Mark Sifford
(74) *Attorney, Agent, or Firm* — Bookoff McAndrews, PLLC

(57) ABSTRACT

Methods for viral clearance using low pH hold based on a statistical design of experiment are provided. Several factors are evaluated to characterize the impacts of a low pH hold step for virus inactivation, including the factors of pH conditions, conductivity conditions, protein type, temperature, acid titrant, spike timing, and post-spike filtration. In addition to the effect of pH on virus inactivation, an increase in ionic strength through manipulating the conductivity can be a key component that influences virus inactivation kinetics.

38 Claims, 21 Drawing Sheets

VIRAL CLEARANCE BY LOW pH HOLD

CROSS-REFERENCE TO RELATED APPLICATION

This application claims priority to and the benefit of U.S. Provisional Patent Application No. 63/023,154 filed May 11, 2020 which is herein incorporated by reference.

The present invention generally pertains to methods for inactivating viral particles in protein sample using a low pH hold step. A statistical design of experiment incorporating several factors is used to evaluate and characterize the impacts of a low pH hold step for virus inactivation.

BACKGROUND

Biological products are susceptible to contamination (both endogenous contaminants and adventitious (coming from external sources) contaminants) from bacteria, fungi and viruses. Viral clearance, for example, viral inactivation, is an important step during the manufacture of biopharmaceutical products produced using mammalian cell lines. Global health authorities require evaluation of viral clearance for manufacturing biologics or biotechnology products, since viral contamination can be amplified during the growth of mammalian cell culture. Effective viral clearance studies are an important part of process validation, which also are important to ensure drug safety. Viral contamination also can affect raw materials, cell culture processes, bioreactor and downstream purification processes.

Viral validation studies are designed to document selected operating conditions regarding product quality to assure viral safety. The experimental design of viral clearance studies includes characterizations of the manufacturing process to identify significant development factors to improve understanding of processing conditions and justify selection of worst-case conditions. The processes of virus inactivation or removal include pH treatment, heat treatment, solvent/detergent treatment, filtration or chromatography. The mechanism of virus inactivation for low pH incubation includes a pH-based chemical reaction causing irreversible denaturation of surface glycoproteins or disruption of the lipid envelope of the virus.

The pH conditions adapted in manufacturing processes of the biopharmaceutical products may not be effective for virus inactivation. However, the pH required for viral inactivation can be significantly different than the pH ranges used in other manufacturing conditions. Using low pH incubation to obtain effective virus inactivation in protein samples is challenging for manufacturing biopharmaceutical products, since the low pH exposure of biopharmaceutical products can alter the quality or stability of proteins. It will be appreciated that a need exists for methods to evaluate and characterize the impact of a low pH hold step for virus inactivation during the manufacturing of biopharmaceutical products. These methods should provide effective and robust experimental designs to ensure virus inactivation for designing a manufacturing process, such as a purification process.

SUMMARY

The present application provides methods for viral clearance using low pH hold based on a statistical design of experiments incorporating several factors to evaluate and characterize the impacts of a low pH hold step for virus inactivation. The statistically designed experiment is used to evaluate the effect of pH conditions, ionic strength conditions, protein isotype, temperature, acid titrant, spike timing, and post-spike filtration on virus inactivation. These methods can be used to predict effective clearance when the viral inactivation step is conducted in the range of about pH 3.60-3.90 by, for example, manipulating ionic strength of the low pH starting material.

This disclosure provides a method for purifying a peptide or protein, such as an antibody, from a sample comprising one or more impurities including viral particles. In some exemplary embodiments, the method of the present application comprises: adjusting an ionic strength condition of the sample, adjusting a pH condition of the sample to an acidic pH, and subsequently maintaining the sample at the ionic strength condition and the pH condition for at least about 15 minutes to inactivate a quantity of viral particles; wherein the sample comprises one or more impurities including the viral particles. In one aspect, the quantity of the viral particle inactivation is at least about 3 LRF (logarithmic reduction factor) for using the method of the present application. In one aspect, the quantity of the viral particle inactivation is at least about 4 LRF for using the method of the present application.

In one aspect, the pH condition of the sample in the method of the present application is less than or equal to about pH 3.90. In one aspect, the pH condition of the sample is in a range of from about pH 3.60 to about pH 3.90. In another aspect, the pH condition of the sample is in a range of from about pH 3.65 to about pH 3.80. In another aspect, the peptide or protein in the sample is an antibody produced in a host-cell. In yet another aspect, the sample in the method of the present application is maintained at the ionic strength condition and the pH condition of the sample for at least about 30 minutes to inactivate the quantity of the viral particles. In one aspect, the sample in the method of the present application is maintained at the ionic strength condition and the pH condition of the sample for from about 15 minutes to about 30 minutes to inactivate the quantity of the viral particles.

In one aspect, the method of the present application further comprises optimizing the inactivation of the quantity of the viral particles by running a D-Optimal design of experiment. In another aspect, the D-Optimal design of experiment evaluates the following factors: the pH condition of the sample, and the salt concentration added to the sample. In one aspect, the D-Optimal design of experiment further evaluates the following factors: a type of the peptide or protein, a temperature of the sample, an acid titrant to adjust the pH condition of the sample, a spike timing for spiking the viral particles to the sample, or a presence of a post-spike filtration.

In one aspect, the sample in the method of the present application is an eluent from protein A chromatography. In another aspect, the ionic strength of the sample is adjusted using an addition of sodium chloride, wherein a concentration of the sodium chloride is in a range of from about 1 mM to about 100 mM, from about 1 mM to about 500 mM, about 25 mM, about 50 mM, about 72 mM, about 82 mM, about 100 mM, about 125 mM, about 150 mM, about 175 mM, or about 200 mM. In one aspect, the pH condition of the sample is adjusted using phosphoric acid or glycine HCl. In another aspect, the peptide or protein in the sample of the method is an antibody having an IgG1 isotype or having an IgG4 isotype. In one aspect, the peptide or protein is a monoclonal antibody or a bispecific antibody. In yet another aspect, the peptide or protein is an antibody, an antibody fragment, a Fab region of an antibody, an antibody-drug conjugate, a fusion protein, a protein pharmaceutical product or a drug.

This disclosure provides a method of producing a preparation comprising a protein of interest and a reduced amount of infectious viral particles from a sample having the protein of interest and an infectious viral particle. In some exemplary embodiments, the method of producing a preparation comprising a protein of interest and a reduced amount of infectious viral particles from a sample having the protein of interest and an infectious viral particle, comprising subjecting the sample to a pH of greater than pH of about 3.60 and ionic strength condition by addition of a salt with a concentration up to about 100 mM; and maintaining the sample at the pH and ionic strength conditions for an appropriate amount of time to produce the preparation comprising the protein of interest and the reduced amount of infectious viral particles.

In one aspect, the concentration of the protein of interest in the sample is less than about 25 g/L.

In one aspect, the appropriate amount of time is about 15 minutes, about 20 minutes, about 25 minutes, or about 30 minutes.

In one aspect, the method reduces the amount of infectious viral particles from a sample at by about 3 LRF (logarithmic reduction factor). In another aspect, the method reduces the amount of infectious viral particles from a sample at by about 4 LRF.

In one aspect, the pH condition of the sample is greater than about pH 3.70. In another aspect, the pH condition of the sample is greater than about pH 3.80. In yet another aspect, the pH condition of the sample is greater than about pH 3.90. In yet another aspect, the pH condition of the sample is greater than about pH 4.0.

In one aspect, the pH condition of the sample is in a range of from about pH 3.60 to about pH 4.0. In another aspect, the pH condition of the sample is in a range of from about pH 3.70 to about pH 4.0. In yet another aspect, the pH condition of the sample is in a range of from about pH 3.80 to about pH 4.0.

Exemplary sources for a "sample" may include an affinity chromatography, such as Protein A eluate; the sample may be obtained from a flow-through fraction of ion exchange chromatography procedure; it may also be obtained from the strip of an ion exchange column—there are other sources during a purification process well known to those skilled in the art from which a sample may be obtained. In one aspect of this embodiment, the sample is an eluent from protein A chromatography.

In one aspect, the ionic strength of the sample is adjusted by using an addition of sodium chloride, wherein a concentration of the sodium chloride is in a range of from about 1 mM to about 200 mM.

In one aspect, the ionic strength condition is adjusted by using a sodium chloride with a concentration of greater than about 50 mM. In another aspect of this embodiment, the concentration is greater than about 100 mM.

In one aspect, the pH condition of the sample is adjusted using phosphoric acid or glycine HCl.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

DETAILED DESCRIPTION

Figure 1A:
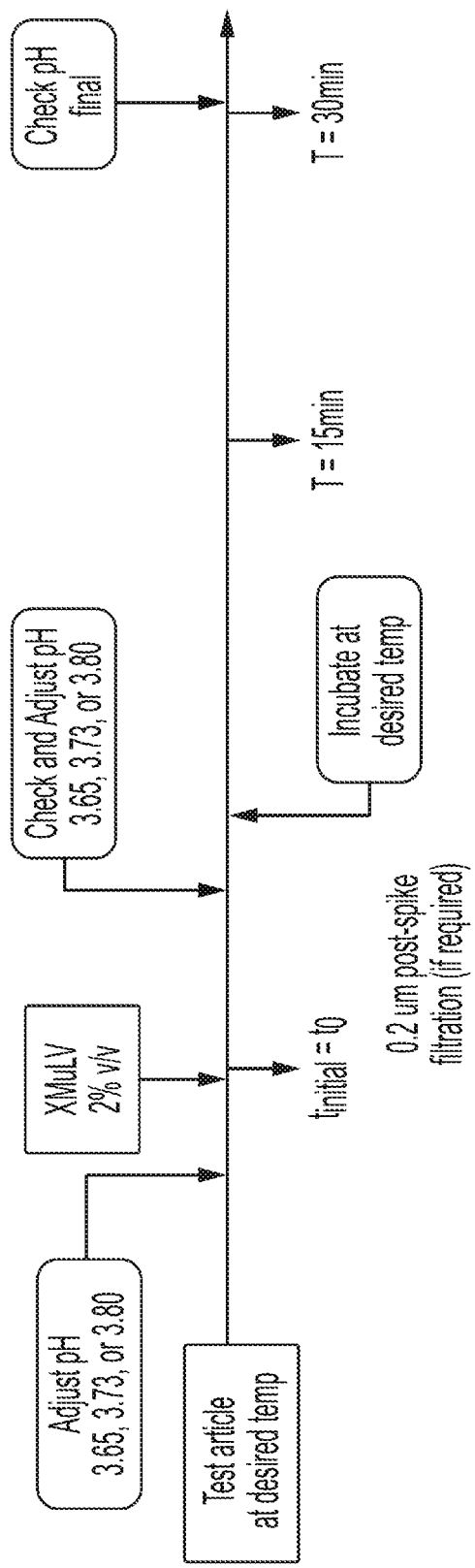
FIG. 1A shows the adjust-spike-readjust method, wherein samples are adjusted/titrated to the target pH then spiked with the virus stock at about pH 7.2 followed by readjusting the pH of the samples to the target pH prior to being held at the desired temperature for the remainder of the pH hold according to an exemplary embodiment. Timing begins at the time of the spike.

Viral clearance is important to manufacturing biopharmaceutical products, especially for biopharmaceutical products which are produced using mammalian cell lines, such as Chinese hamster ovary (CHO) cells. It is important to ensure viral clearance for designing a purification process. Typical workflow for studying viral clearance of a manufacturing process includes spiking the sample load with virus, running the process on a scale-down experiment to mimic a large-scale step and documenting the ability to clear the spiked virus. The processes of virus inactivation or removal include pH treatment, heat treatment, solvent/detergent treatment, filtration or chromatography. The evaluation of viral clearance should include demonstrating removal of a specific model virus for retrovirus-like particles, which are inherent in the genome of CHO cells (Anderson et al., Endogenous origin of defective retrovirus-like particles from a recombinant Chinese hamster ovary cell line, Virology 181(1): 305-311, 1991). Retrovirus is an enveloped RNA virus that is propagated in a host cell using the reverse transcriptase enzyme to produce DNA from its RNA genome. The produced DNA is then incorporated into the host's genome for replication. Xenotropic murine leukemia virus (X-MuLV) can be used as a model virus in the evaluation of virus inactivation in CHO cell-derived pharmaceutical proteins. Murine Leukemia virus (MuLV) is a retrovirus and has a positive single-stranded sense RNA that replicates via reverse transcription. MuLV can induce leukemia in inoculated mice.

Viral reduction or viral clearance refers to the difference between the total virus amounts or infectious virus amounts in the input sample and output sample after performing the specific process step, such as a chromatography process. The viral reduction capability can be defined as the logarithmic reduction value (LRV) or logarithmic ($\log_{10}$) reduction factor (LRF) of a process step. The reduction factor is calculated based on the total virus load before applying the clearance step and the total virus amount after applying the clearance step. Viral validation studies can be conducted to document clearance of known viruses associated with the product and to estimate the effectiveness of the process to clear potential adventitious viral contaminants by characterizing the ability of the process to clear non-specific model viruses.

The present application provides a statistically designed experiment which can be used to evaluate and characterize the effects of a low pH hold step for virus inactivation including the evaluation of several factors, such as protein isotype, pH condition, temperature, acid titrant, ionic strength condition, spike timing, or post-spike filtration. These methods can be used to predict effective clearance when the viral inactivation step is conducted in the range of about pH 3.60-3.90 by manipulating ionic strength by increasing conductivity of the low pH starting material. Models generated from the experiments can be used to predict clearance of viruses, such as X-MuLV, over a range of process conditions at different time points, such as at about 15 minutes and about 30 minute time points. In some exemplary embodiments, in addition to the effect of pH conditions on virus inactivation, increasing the conductivity of the starting solution can increase virus inactivation. For example, an increase in sodium chloride (NaCl) concentration can be a key component that influences virus inactivation kinetics to achieve greater virus inactivation. In one aspect, the present application provides the advantages of robust and effective inactivation of viruses, such as greater than about 4 LRF for the inactivation of X-MuLV, which can be achieved through an increase in ionic strength of the low pH starting material.

In accordance with ICH Q5A (R1) (Viral safety evaluation of biotechnology products derived from cell lines of human or animal origin. International Conference on Harmonization of Technical Requirements for Registration of Pharmaceuticals for Human Use. Current Step 4 version, Sep. 23, 1999), downstream purification processes of biopharmaceutical products are developed to ensure removal and/or inactivation of endogenous or adventitious virus contaminants. Typical downstream purification processes can incorporate several orthogonal virus clearing steps, including one dedicated step to inactivate enveloped viruses. Low pH incubation can be used to inactivate enveloped viruses, such as irreversible denaturation of capsids (Brorson et al., Bracketed generic inactivation of rodent retroviruses by low pH treatment for monoclonal antibodies and recombinant proteins, Biotechnol Bioeng 82(3): 321-329, 2003). Filtration is a size-based removal which can be used to remove both enveloped and non-enveloped viruses (Lute et al., Phage passage after extended processing in small-virus-retentive filters, Biotechnol Appl Biochem 47(Pt 3): 141-151, 2007). Chromatography steps can be used to purify biologics products with a potential to provide viral reduction for viral clearance, such as the use of protein A chromatography (Bach et al., Clearance of the rodent retrovirus, XMuLV, by protein A chromatography, Biotechnol Bioeng 112(4): 743750, 2015) or anion exchange chromatography (Strauss et al., Anion exchange chromatography provides a robust, predictable process to ensure viral safety of biotechnology products, Biotechnol Bioeng 102(1): 168-175, 2009a).

Low pH virus inactivation is commonly executed after the protein A capture step to inactivate viruses during the purification of biopharmaceutical products, such as monoclonal antibodies. The product eluted from protein A chromatography is typically at a low pH, which is further acidified and held for at least 30 minutes for virus inactivation. The mechanism of virus inactivation is primarily through a pH-based chemical reaction causing irreversible denaturation of surface glycoproteins or disruption of the lipid envelope of the virus (Brorson et al., supra). Upon completion of the pH hold, the product is neutralized and advanced to further downstream processing. The low pH step has been observed to reliably produce 4 LRF of large enveloped viruses (Miesegaes et al., Analysis of viral clearance unit operations for monoclonal antibodies. Biotech Bioeng. 2019; 106:238-246). Previous studies indicate that ionic strength may affect the inactivation kinetics of X-MuLV. The experiment conditions having increased ionic strength, such as higher buffer concentrations or higher protein concentrations with titration of a weak acid, can correlate with higher LRVs at pH 3.7 and 3.8 (Chinniah et al., Characterization of operating parameters for XMuLV inactivation by low pH treatment, Biotechnol Prog, 2016. January-February; 32,(1), 89-97, doi: 10.1002/btpr.2183. Epub 2015 Nov. 5).

Studies have been done to understand viral clearance by low pH hold. These studies support a pH based chemical reaction affected by pH, time, and temperature (Brorson et al.). Because the inactivation step is robust, Brorson et al. has developed a "bracketed generic clearance" where low-pH inactivation is performed at pH conditions of less than or equal to pH 3.8 and at temperatures of greater than or equal to 14° C. for a minimum of 30 minute hold to achieve consistently greater than or equal to 4.6 log 10 clearance of X-MuLV. ASTM (American Society for Testing and Materials) further reduced the operating space of low pH hold to less than or equal to pH 3.6 and temperature of greater than or equal to 15° C. to achieve greater than or equal to 5.0 LRF according to ASTM E2888-12 (ASTM. E2888-12: Standard Practice for Process for Inactivation of Rodent Retrovirus by pH. West Conshohocken, PA: ASTM International; 2012. www.astm.org). Furthermore, according to ASTM E2888-12, the hold time is equal to or greater than 30 minutes.

Over time, guidance has been revised to reduce the pH of the hold in order to achieve greater LRFs. To claim the generic clearance provided by ASTM E2888-12, the protein of interest should fit into the generic mold the document defines. Effective virus inactivation can be especially challenging for biopharmaceutical products, such as monoclonal antibodies, since the exposure of proteins to low pH can alter the quality or stability of proteins. Health authorities expect low pH hold to be validated under worst case conditions. It indicates that the retrovirus inactivation is determined at a pH condition which is above the actual manufacturing range. Viral clearance can be compromised when the inactivation step is operated outside of these ranges.

In some exemplary embodiments, the present application provides a statistically designed experiment, for example, experimental design, including controlled and uncontrolled factors related to the low pH inactivation step to determine the impact of protein type, pH condition, temperature, acid titrant, NaCl content, spike timing, or post-spike filtration on virus inactivation at different time points. In some aspects, the present application provides experimental factors and conditions to define operating conditions for reliable and effective virus clearance. In some aspects, X-MuLV is selected as the model endogenous enveloped virus. In some aspects, two types of monoclonal antibodies, such as IgG1 or IgG4, are subjected to testing various parameters, such as pH, temperature, acid titrant, ionic strength, spike timing, or filtration post-spike.

The experimental design, for example, design of experiments or DoE, of the present application for multivariate analysis includes characterizations of virus inactivation at low pH hold. DoE is a methodology which allows systematic variations of multiple development factors within the context of one experimental design. The results of DoE can be used to create mathematical models of the process being examined. The true optimum of the examined process can be identified by applying these mathematical models. Applications of DoE results include eliminating insubstantial development factors, identifying important development factors for further study and predicting the performance of examined process. DoE is conducted in a systematic logical flow including stating objectives, selecting variable factors and models, creating experimental designs to support the models, collecting data based on the designs, executing the analysis, or verifying the models with check points and reporting the outcomes. The results of DoE and resultant models can be used to confirm, reject, or alter existing understanding of the mechanism of low pH hold for viral clearance.

In some exemplary embodiments, the present application provides a method for purifying an antibody from a sample comprising one or more impurities including potentially infectious viral particles, wherein the method of the present application comprises: adjusting an ionic strength condition of the sample, adjusting a pH condition of the sample to an acidic pH, and subsequently maintaining the sample at the ionic strength condition and the pH condition for at least about 15 minutes to inactivate a quantity of viral particles. In one aspect, a capability of the method of the present application for inactivating the quantity of the viral particles is at least about 3 LRF. In one aspect, a capability of the method of the present application for inactivating the quantity of the viral particles is at least about 4 LRF. In one aspect, the peptide or protein in the sample is an antibody produced in a host-cell. In one aspect, the antibody is a monoclonal antibody or a bispecific antibody. In one aspect, the antibody in the method of the present application is an eluent from protein A chromatography.

In one aspect, the pH condition of the sample in the method of the present application is less than or equal to about pH 3.90. In one aspect, the pH condition of the sample is in a range of from about pH 3.60 to about pH 3.90. In one aspect, the pH condition of the sample is in a range of from about pH 3.65 to about pH 3.80. In some aspects, the pH condition in the statistically designed experiment of the present application is in the range of from about pH 3.65 to about pH 3.80, such as at about pH 3.65, about pH 3.73, or about pH 3.80, which is equal to or greater than the pH range of the manufacturing processes. The pH range of pH 3.65-3.80 is greater than and outside of the pH range suggested by ASTM E2888-12, for example, less than or equal to pH 3.6. It is known that lower pH conditions can cause faster virus inactivation (Brorson et al.). In some aspects, the temperature in the statistically designed experiment of the present application is in the range of from about 15° C. to about 20° C., such as about 15° C. or about 20° C., which is on the lower end or less than the temperature range of the manufacturing processes. It is known that higher temperature can cause faster inactivation (Brorson et al.). The temperature range of from about 15° ° C. to about 20° C. is within the temperature range suggested by ASTM E2888-12, for example, greater or equal to 15° C. In some aspects, the acid titrant in the statistically designed experiment of the present application is about 0.25 M phosphoric acid or about 0.25 M glycine HCl. In some aspects, the NaCl content added to the starting material in the statistically designed experiment of the present application is in the concentration range of from about 0 mM to about 100 mM.

Figure 1B:
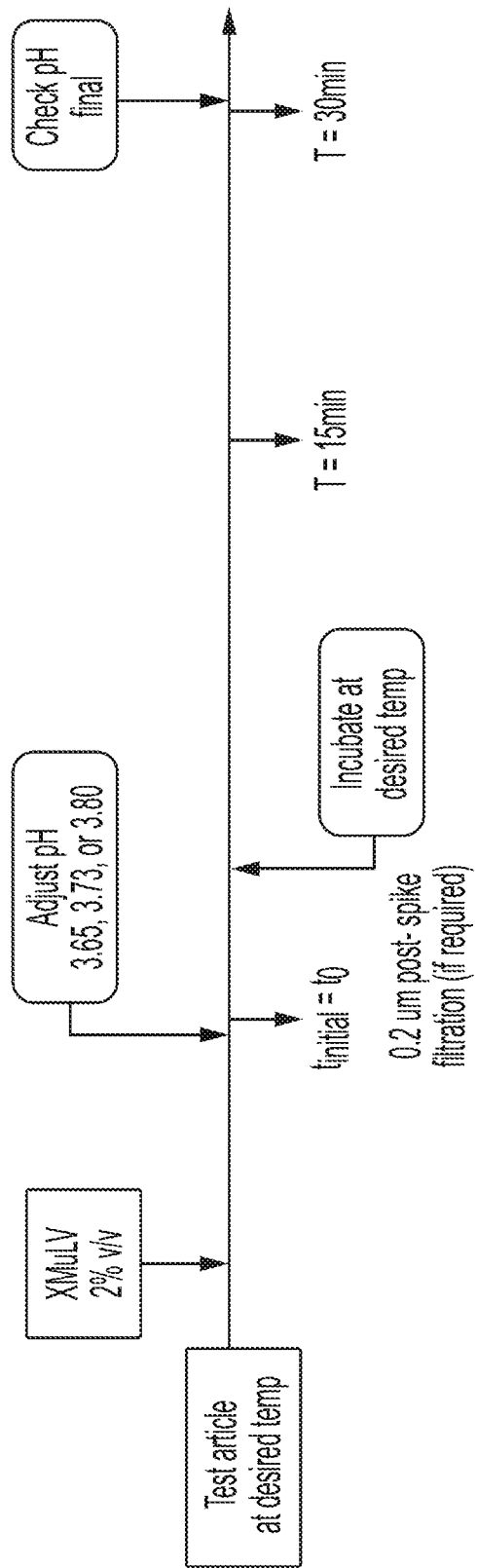
FIG. 1B shows the spike-adjust method, wherein samples are first spiked with the virus stock solution then adjusted/titrated to the target pH according to an exemplary embodiment. Timing begins at the time the target pH of the sample is reached.

In some aspects, the method of the present application further comprises optimizing the inactivation of a quantity of the viral particles by running a D-Optimal DoE to evaluate various factors, including the pH condition of the sample, the conductivity of the sample, a type of the peptide or protein, a temperature of the sample, an acid titrant to adjust the pH condition of the sample, a spike timing for spiking the viral particles to the sample, or a presence of a post-spike filtration. In some aspects, the spiking timing in the statistically designed experiment of the present application is an adjust-spike-readjust method or a spike-adjust method. The adjust-spike-readjust method can provide constant desirable pH range during the entire hold time. The spike-adjust method can represent authentic manufacturing conditions, where in-process intermediate containing endogenous retrovirus-like particles is acidified from a starting pH. Under the adjust-spike-readjust method as shown in FIG. 1A, samples are adjusted/titrated to the target pH then spiked with the virus stock having about pH 7.2. Timing of the pH hold began at the time of spiking. Due to the observation of pH increases after spiking virus stock, the pH of the samples were readjusted to the target pH prior to being held at the desired temperature for the remainder of the pH hold. Under the spike-adjust method as shown in FIG. 1B, samples are first spiked with the virus stock solution then adjusted/titrated to the target pH. When the target pH is reached, timing of the pH hold started, and the sample is incubated at the desired temperature. In some aspects of the statistically designed experiment of the present application, the low pH hold can be conducted with or without post-spike filtration using a filter, such as an about 0.2 μm filter. The post-spike filtration represents authentic manufacturing operation where in-process intermediate containing endogenous retrovirus-like particles is filtered to maintain sterility. The filtration step can result in monodispersed virus, which may remove virus aggregates.

In some exemplary embodiments, the conductivity of the starting material has a strong effect on impacting virus inactivation kinetics at different target pH conditions. In some exemplary embodiments, the present application provides models to predict viral clearance over a range of process conditions. In some aspects, in addition to the effect of pH on virus inactivation, an increase in ionic strength or conductivity, such as NaCl concentration, can be a key component that influences virus inactivation kinetics. In one aspect, the pH condition is an important factor when the load material has low ionic strength. For example, X-MuLV inactivation can be dependent on pH conditions at low ionic strength. In some aspects, when the ionic strength is increased, the influence of pH conditions on virus inactivation decreased. For example, X-MuLV can be rapidly inactivated at all target pH conditions, when the ionic strength increased. In some aspects, when about 50 mM or about 100 mM NaCl is present, complete and effective viral clearance, such as inactivation of X-MuLV, is observed at about 30 minute time points for target pH conditions at about pH 3.65, about pH 3.73, and about pH 3.80. For pH conditions at about pH 3.65 and pH 3.73, complete inactivation of X-MuLV was observed after 15 minutes. In one aspect, the ionic strength of the sample is adjusted using an addition of sodium chloride, wherein a concentration of the sodium chloride is in a range of from about 1 mM to about 100 mM, from about 1 mM to about 500 mM, about 50 mM, or about 100 mM.

Low pH hold during the manufacturing of biopharmaceutical products can have important impacts on the quality and stability of the proteins, such as monoclonal antibodies. The models of the present application can be used to predict effective clearance when viral inactivation is operated in the range of pH 3.60 to pH 3.90 by manipulating the conductivity of the low pH starting material. In some aspects, the present application provides that increasing the conductivity through the addition of NaCl to the starting material can achieve rapid and effective virus inactivation at various target pH conditions. In one aspect, the sample in the method of the present application is maintained at the ionic strength condition and the pH condition of the sample for at least about 30 minutes to inactivate the quantity of the viral particles. In one aspect, the sample in the method of the present application is maintained at the ionic strength condition and the pH condition of the sample for from about 15 minutes to about 30 minutes to inactivate the quantity of the viral particles.

The testing results of the statistical DoE for low pH hold in the present application are consistent with the ASTM standard for 5.0 LRF X-MuLV inactivation at pH less than about 3.60. The results also demonstrate robust and effective inactivation at pH greater than about 3.60. For ranges outside the ASTM generic claim, the results indicate that increasing the NaCl content can achieve rapid and effective X-MuLV inactivation. Typically, pH of the hold is dependent on the stability of the protein. The models of the present application provide the advantage of predicting effective clearance when operating between pH 3.60 and pH 3.90 by manipulating the conductivity of the low pH starting material.

The demands of improving the product quality, efficacy and safety of biopharmaceutical products have led to an increasing demand for effective and robust experimental designs to ensure virus inactivation. This disclosure provides methods to satisfy the aforementioned demands. Exemplary embodiments disclosed herein satisfy the aforementioned demands by providing methods for purifying an antibody from a sample comprising one or more impurities including viral particles. The present application provides robust and effective inactivation of viruses through an increase in ionic strength of the low pH starting material and models to predict effective clearance at any operating pH by manipulating ionic strength of the low pH starting material to satisfy the long felt needs.

The term "a" should be understood to mean "at least one"; and the terms "about" and "approximately" should be understood to permit standard variation as would be understood by those of ordinary skill in the art; and where ranges are provided, endpoints are included. As used herein, the terms "include," "includes," and "including," are meant to be non-limiting and are understood to mean "comprise," "comprises," and "comprising," respectively.

In some exemplary embodiments, the present application provides a method for purifying a peptide or protein, such as an antibody, from a sample comprising one or more impurities including viral particles. In some exemplary embodiments, the method of the present application comprises: adjusting an ionic strength condition of the sample, adjusting a pH condition of the sample to an acidic pH, and subsequently maintaining the sample at the ionic strength condition and the pH condition for at least about 15 minutes to inactivate a quantity of viral particles. In one aspect, the peptide or protein in the sample is an antibody produced in a host-cell. In one aspect, the peptide or protein is a monoclonal antibody or a bispecific antibody. In one aspect, the peptide or protein is an antibody, an antibody fragment, a Fab region of an antibody, an antibody-drug conjugate, a fusion protein, a protein pharmaceutical product or a drug.

As used herein, the term "protein" or "protein of interest" can include any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides' refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may comprise one or multiple polypeptides to form a single functioning biomolecule. Another exemplary aspect, a protein can include antibody fragments, nanobodies, recombinant antibody chimeras, cytokines, chemokines, peptide hormones, and the like. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. Proteins may be produced using recombinant cell-based production systems, such as the insect baculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," (Darius Ghaderi et al., Production platforms for biotherapeutic glycoproteins. Occurrence, impact, and challenges of non-human sialylation, 28 BIOTECHNOLOGY AND GENETIC ENGINEERING REVIEWS 147-176 (2012)). In some exemplary embodiments, proteins comprise modifications, adducts, and other covalently linked moieties. These modifications, adducts and moieties include, for example, avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

In some exemplary embodiments, the protein of interest can be a recombinant protein, an antibody, a bispecific antibody, a multispecific antibody, antibody fragment, monoclonal antibody, fusion protein, scFv and combinations thereof.

As used herein, the term "recombinant protein" refers to a protein produced as the result of the transcription and translation of a gene carried on a recombinant expression vector that has been introduced into a host cell. In certain exemplary embodiments the recombinant protein can be a fusion protein. In certain exemplary embodiments the recombinant protein can be an antibody, for example, a chimeric, humanized, or fully human antibody. In certain exemplary embodiments the recombinant protein can be an antibody of an isotype selected from group consisting of: IgG (e.g., IgG1, IgG2, IgG3, IgG4), IgM, IgA1, IgA2, IgD, or IgE. In certain exemplary embodiments the antibody molecule is a full-length antibody (e.g., an IgG1 or IgG4 immunoglobulin) or alternatively the antibody can be a fragment (e.g., an Fc fragment or a Fab fragment).

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. In different embodiments of the invention, the FRs of the anti-big-ET-1 antibody (or antigen-binding portion thereof) may be identical to the human germline sequences or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, for example, from full antibody molecules using any suitable standard techniques such as proteolytic digestion or recombinant genetic engineering techniques involving the manipulation and expression of DNA encoding antibody variable and optionally constant domains. Such DNA is known and/or is readily available from, for example, commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment comprises a sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively, or additionally, an antibody fragment may be wholly or partially synthetically produced. An antibody fragment may optionally comprise a single chain antibody fragment. Alternatively, or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

The phrase "bispecific antibody" includes an antibody capable of selectively binding two or more epitopes. Bispecific antibodies generally comprise two different heavy chains, with each heavy chain specifically binding a different epitope-either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain.

A typical bispecific antibody has two heavy chains each having three heavy chain CDRs, followed by a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bsAbs can have different formats, such as, but not limited to, triomab, knobs into holes IgG (kih IgG), crossMab, orth-Fab IgG, Dual-variable domains Ig (DVD-Ig), Two-in-one or dual action Fab (DAF), IgG-single-chain Fv (IgG-scFv), or κλ-bodies. The non-IgG-like different formats include tandem scFvs, diabody format, single-chain diabody, tandem diabodies (Tand-Abs), Dual-affinity retargeting molecule (DART), DART-Fc, nanobodies, or antibodies produced by the dock-and-lock (DNL) method (Gaowei Fan, Zujian Wang & Mingju Hao, Bispecific antibodies and their applications, 8 JOURNAL OF HEMATOLOGY & ONCOLOGY 130; Dafne Müller & Roland E. Kontermann, Bispecific Antibodies, HANDBOOK OF THERAPEUTIC ANTIBODIES 265-310 (2014)). The methods of producing BsAbs are not limited to quadroma technology based on the somatic fusion of two different hybridoma cell lines, chemical conjugation, which involves chemical cross-linkers, and genetic approaches utilizing recombinant DNA technology. Examples of bsAbs include those disclosed in the following patent applications, which are hereby incorporated by reference: U.S. Ser. No. 12/823,838, filed Jun. 25, 2010; U.S. Ser. No. 13/488,628, filed Jun. 5, 2012; U.S. Ser. No. 14/031,075, filed Sep. 19, 2013; U.S. Ser. No. 14/808,171, filed Jul. 24, 2015; U.S. Ser. No. 15/713,574, filed Sep. 22, 2017; U.S. Ser. No. 15/713,569, field Sep. 22, 2017; U.S. Ser. No. 15/386,453, filed Dec. 21, 2016; U.S. Ser. No. 15/386,443, filed Dec. 21, 2016; U.S. Ser. No. 15/22,343 filed Jul. 29, 2016; and U.S. Ser. No. 15/814,095, filed Nov. 15, 2017. Low levels of homodimer impurities can be present at several steps during the manufacturing of bispecific antibodies. The detection of such homodimer impurities can be challenging when performed using intact mass analysis due to low abundances of the homodimer impurities and the co-elution of these impurities with main species when carried out using a regular liquid chromatographic method.

As used herein "multispecific antibody" or "Mab" refers to an antibody with binding specificities for at least two different antigens. While such molecules normally will only bind two antigens (i.e., bispecific antibodies, BsAbs), antibodies with additional specificities such as trispecific antibody and KIH Trispecific can also be addressed by the system and method disclosed herein.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

In some exemplary embodiments, the protein of interest can be purified from mammalian cells. The mammalian cells can be of human origin or non-human origin can include primary epithelial cells (e.g., keratinocytes, cervical epithelial cells, bronchial epithelial cells, tracheal epithelial cells, kidney epithelial cells and retinal epithelial cells), established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LSI80 cells, LS174T cells, NCI-H-548 cells, RPMI2650 cells, SW-13 cells, T24 cells, WI-28 VA13, 2RA cells, WISH cells, BS-C-I cells, LLC-MK2 cells, Clone M-3 cells, 1-10 cells, RAG cells, TCMK-1 cells, Y-1 cells, LLC-PKi cells, PK(15) cells, GHi cells, GH3 cells, L2 cells, LLC-RC 256 cells, MHiCi cells, XC cells, MDOK cells, VSW cells, and TH-I, B1 cells, BSC-1 cells, RAf cells, RK-cells, PK-15 cells or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, Midi cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDMiC3 cells, KLN205 cells, McCoy cells, Mouse L cells, Strain 2071 (Mouse L) cells, L-M strain (Mouse L) cells, L-MTK' (Mouse L) cells, NCTC clones 2472 and 2555, SCC-PSA1 cells, Swiss/3T3 cells, Indian muntjac cells, SIRC cells, Cn cells, and Jensen cells, Sp2/0, NS0, NS1 cells or derivatives thereof).

In some exemplary embodiments, the protein of interest can be a VEGF antagonist. As used herein, a "VEGF antagonist" is any agent that binds to or interacts with VEGF, inhibits the binding of VEGF to its receptors (VEGFR1 and VEGFR2), and/or inhibits the biological signaling and activity of VEGF. VEGF antagonists include molecules, which interfere with the interaction between VEGF and a natural VEGF receptor, for example, molecules which bind to VEGF or a VEGF receptor and prevent or otherwise hinder the interaction between VEGF and a VEGF receptor. Specific exemplary VEGF antagonists include anti-VEGF antibodies (e.g., ranibizumab [LUCENTIS®]), anti-VEGF receptor antibodies (e.g., anti-VEGFR1 antibodies, anti-VEGFR2 antibodies, etc.), and VEGF receptor-based chimeric molecules or VEGF-inhibiting fusion proteins (also referred to herein as "VEGF-Traps" or "VEGF Mini-Traps"), such as aflibercept, ziv-aflibercept and a protein having an amino acid having SEQ ID NO.: 42. Other examples of VEGF-Traps are ALT-L9, M710, FYB203 and CHS-2020. Additional examples of VEGF-Traps can be found in U.S. Pat. Nos. 7,070,959; 7,306,799; 7,374,757; 7,374,758; 7,531,173; 7,608,261; 5,952,199; 6,100,071; 6,383,486; 6,897,294 & 7,771,721, which are specifically incorporated herein by reference in their entirety.

VEGF receptor-based chimeric molecules include chimeric polypeptides which comprise two or more immunoglobulin (Ig)-like domains of a VEGF receptor such as VEGFR1 (also referred to as Flt1) and/or VEGFR2 (also referred to as Flk1 or KDR), and may also comprise a multimerizing domain (e.g., an Fc domain which facilitates the multimerization such as dimerization of two or more chimeric polypeptides). An exemplary VEGF receptor-based chimeric molecule is a molecule referred to as VEGFR1R2-FcΔC1(a) (also known as aflibercept; marketed under the product name EYLEA®).

As used herein, the term "protein pharmaceutical product" includes an active ingredient which can be fully or partially biological in nature. In some exemplary embodiments, the protein pharmaceutical product can comprise a peptide, a protein, a fusion protein, an antibody, an antigen, vaccine, a peptide-drug conjugate, an antibody-drug conjugate, a protein-drug conjugate, cells, tissues, or combinations thereof. In some other exemplary embodiments, the protein pharmaceutical product can comprise a recombinant, engineered, modified, mutated, or truncated version of a peptide, a protein, a fusion protein, an antibody, an antigen, vaccine, a peptide-drug conjugate, an antibody-drug conjugate, a protein-drug conjugate, cells, tissues, or combinations thereof.

Exemplary Embodiments

Embodiments disclosed herein provide methods for purifying a peptide or protein, such as an antibody, from a sample comprising one or more impurities including viral particles. Embodiments disclosed herein also provide methods for viral clearance using low pH hold based on a statistical design of experiment.

In some exemplary embodiments, the present application provides a method for purifying a peptide or protein, such as an antibody, from a sample comprising one or more impurities including viral particles. In some exemplary embodiments, the method of the present application comprises: adjusting an ionic strength condition of the sample, adjusting a pH condition of the sample to an acidic pH, and subsequently maintaining the sample at the ionic strength condition and the pH condition for at least about 15 minutes to inactivate a quantity of viral particles.

In one aspect, the pH condition of the sample in the method of the present application is an acidic pH, less than or equal to about pH 7, less than or equal to about pH 6, less than or equal to about pH 5, less than or equal to about pH 4, less than or equal to about pH 3.90, less than or equal to about pH 3.80, less than or equal to about pH 3.70, from about pH 3.60 to about pH 3.90, or from about pH 3.65 to about pH 3.80.

In one aspect, the sample in the method of the present application is maintained at the ionic strength condition and the pH condition of the sample to inactivate the quantity of the viral particles for at least about 30 minutes, at least about 15 minutes, from about 15 minutes to about 30 minutes, at least about 10 minutes, at least about 20 minutes, at least about 25 minutes, at least about 35 minutes, from about 10 minutes to about 30 minutes, from about 15 minutes to about 35 minutes, from about 20 minutes to about 30 minutes, from about 20 minutes to about 35 minutes, or from about 25 minutes to about 40 minutes.

In one aspect, the ionic strength of the sample is adjusted using an addition of sodium chloride, wherein a concentration of the sodium chloride is in a range of from about 1 mM to about 200 mM, from about 1 mM to about 500 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 72 mM, about 80 mM, about 82 mM, about 90 mM, about 100 mM, about 150 mM, about 200 mM, about 250 mM, about 300 mM, about 350 mM, about 400 mM, about 450 mM, or about 500 mM.

It is understood that the method is not limited to any of the aforesaid peptide, protein, antibody, D-Optimal design of experiment, virus, retrovirus, virus inactivation, viral clearance, ionic strength or pH conditions.

The consecutive labeling of method steps as provided herein with numbers and/or letters is not meant to limit the method or any embodiments thereof to the particular indicated order. Various publications, including patents, patent applications, published patent applications, accession numbers, technical articles and scholarly articles are cited throughout the specification. Each of these cited references is incorporated by reference, in its entirety and for all purposes, herein. Unless described otherwise, all technical and scientific terms used herein have the same meaning as commonly understood by one of ordinary skill in the art to which this invention belongs. This disclosure will be more fully understood by reference to the following Examples, which are provided to describe this disclosure in greater detail. They are intended to illustrate and should not be construed as limiting the scope of this disclosure.

EXAMPLES

Material and Reagents

1. Model Proteins and Buffers

Different isotypes of monoclonal antibodies which were expressed in CHO cells were used as model proteins, mAb 1 indicating IgG4 isotype and mAb 2 indicating IgG1 isotype. The isoelectric point of the model proteins were estimated to be 8.8 for mAb 1 and pH 9.3 for mAb 2. The monoclonal antibodies were purified using standard protein A chromatography and eluted with 40 mM acetic acid, resulting in a pool at approximately pH 4.2. The concentrations of the monoclonal antibodies were at approximately 15 g/L.

2. Virus Stocks for Spiking and Infectivity Assay

X-MuLV was used for evaluating virus inactivation. X-MuLV virus stocks were prepared by WuXi AppTec (Philadelphia, PA). One lot of X-MuLV virus stock solution had a titer of approximately $10^7$ PFU/mL. For all runs, the virus stock solutions were sonicated and filtered prior to being spiked into the load material. Infectivity samples were removed and analyzed at the time point of 15 minutes, which had the assay volume of 0.5 mL. Infectivity samples were removed and tested at the time point of 30 minute, which had a larger assay volume of 7 mL. All samples were quantified for X-MuLV infectivity using PG4 indicator cells. Prior to plating, samples were neutralized to pH 6.5-7.5. Virus LRF was calculated by comparing the amount of spiked virus present in the load and the amount of virus present in the pool, as described in Equation 1, wherein C(virus,load) indicates virus concentration in the load, C(virus,pool) indicates virus concentration in the pool, V(load) indicates load volume, and V(pool) indicates pool volume.

Equation 1. Calculation of Virus $\mathrm{Log}_{10}$ Reduction Factor (LRF)

$$LRF = \log_{10} \frac{C_{virus,load} \times V_{load}}{C_{virus,pool} \times V_{pool}}$$

Samples were evaluated for cytotoxic effects of the sample matrix on the indicator cell line of the infectivity assay preceding execution of the study. Additional controls were performed during the spiking study to ensure that inactivation of virus has occurred due to the presence of low pH hold and was not associated with the protein matrix itself.

Methods and Devices

1. Methods for pH Titration and Spiking:

Samples were titrated to desired pH values using either 0.25 M phosphoric acid or 0.25 M glycine HCl. The acidic samples were neutralized using 2 M Tris base. Each inactivation experiment was performed using one of two spiking methods as guided by the experimental design. Under spiking method 1, for example, the adjust-spike-readjust method, samples were adjusted/titrated to the target pH then spiked with the virus stock having pH of about 7.2. Timing of the pH hold began at the time of spiking. Due to the observation of pH increases after spiking virus stock, the pH of the samples were readjusted to the target pH prior to being held at the desired temperature for the remainder of the pH hold. Under spiking method 2, for example, the spike-adjust method, samples were first spiked with the virus stock solution then adjusted/titrated to the target pH. The acid addition was performed using a syringe pump with appropriate mixing time and speed to be representative of large-scale manufacturing. When the target pH was reached, timing of the pH hold started, and the sample was incubated at the desired temperature.

For both spiking method 1 and 2, the starting load material was spiked with 2% X-MuLV virus stock (v/v). When post-spike filtration was indicated as a factor in the experiment design, a 0.2 μm PES filter (polyethersulfone filter) was used. The bulk material was incubated in a water bath for the duration of the pH hold. The temperature of the water bath was a factor in the experiment design, which was monitored using a calibrated thermometer. All pH measurements were made offline with a 2 mL sample removed from the bulk material in a biosafety cabinet.

2. Device for pH Measurements

The measurements of pH values were performed using an In Lab Expert Pro pH probe and a SEVENCOMPACT™ S220 pH meter (METTLER TOLEDO®, Columbus, OH), which is a pH, oxidation-reduction potential (ORP), and ion meter. The meter was set to linear calibration mode, strict endpoint format, and automatic temperature compensation. The pH meter is set to display results to two decimal places. The probe was equilibrated in electrode storage solution for 30 to 60 minutes prior to use. The probe was calibrated using buffers having pH 1.68, pH 4.01, or pH 7.00 (VWR®, Radnor, PA). The criteria for the 3-point calibration slope percentage was within the range of 97.0-103.0%. Following a successful calibration, independent buffer standards at pH 3.00 and pH 6.00 were measured to confirm accuracy to be within ±0.03 pH units of the buffer pH. Independent standards were re-measured to confirm that the pH was remained at the target pH following completion of the final sample each day. A new pH probe was calibrated matching the same criterial and used for each day of study execution to minimize probe variability over time.

3. Statistical Design of Experiment (DoE) for Low pH Hold

Figure 2A:
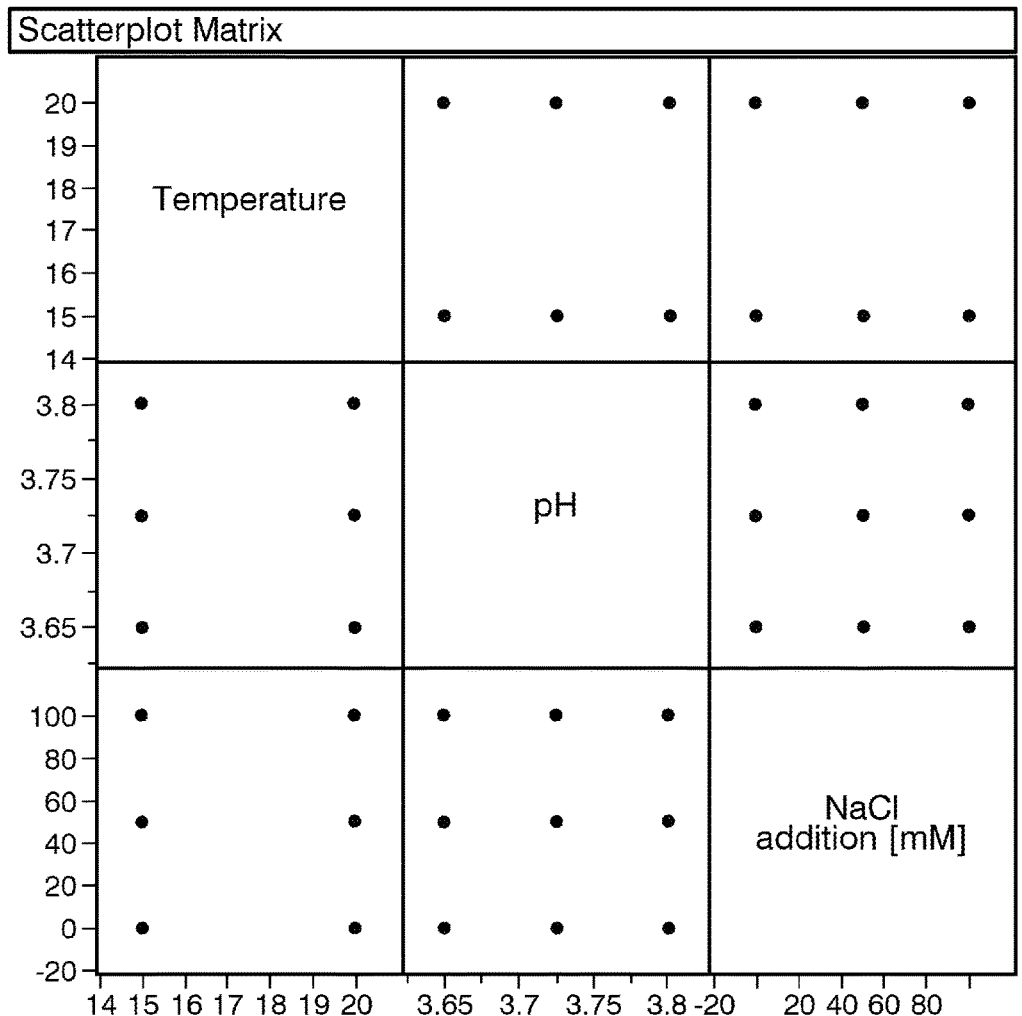
FIG. 2A shows the scatterplot matrix and multivariate correlations of the D-optimal model design to investigate the effects of several factors associated with the low pH hold step for virus inactivation according to an exemplary embodiment.

A statistical design of experiment (DoE) was used to evaluate and characterize the effects of a low pH hold step for retrovirus inactivation. The effects of several factors associated with the low pH hold step were evaluated, including protein type, pH, temperature, acid titrant, NaCl content, spike timing, and post-spike filtration. Software was used to design the statistical DoE to investigate the impacts of these factors. A D-optimal model design, such as 15 runs or 30 runs, was generated using JMP software v.13 (SAS, Cary NC). The scatterplot matrix and multivariate correlations of the D-optimal design are shown in FIG. 2A. Seven factors as shown in Table 1 were built into the study design including: protein type, such as two monoclonal antibodies (mAb) of different isotypes, for example, IgG1 or IgG4; pH, such as pH 3.65, pH 3.73 or pH 3.80; temperature, such as 15° C. or 20° C.; acid titrant, such as 0.25 M phosphoric acid or 0.25 M glycine HCl; NaCl content in starting solution, such as 0 mM, 50 mM, or 100 mM; spike timing, such as the adjust-spike-readjust method or the spike-adjust method;

and post-spike filtration, for example, with or without post-spike filtration. The spiking solution contains X-MuLV purified stock for 2% v/v spike. Table 1 shows the implementation of these seven factors to the design matrix including the specific level or type of each factor.

TABLE 1

Factors used in the design of experiment

| Factor | Level or Type | | |
|---|---|---|---|
| | Low | Center | High |
| mAb isotype | IgG4 | | IgG1 |
| pH | 3.65 ± 0.02 | 3.73 ± 0.02 | 3.80 ± 0.02 |
| Temperature (° C.) | 15 ± 1.0 | | 20 ± 1.0 |
| Acid titrant | Phosphoric | | Glycine HCl |
| Added (mM) | 0 | 50 | 100 |
| Spike timing | Method 1 | | Method 2 |
| Post-spike filtration | Yes | | No |

The design evaluated all main effects and some interactions. A total of 30 runs, 15 conditions with 2 replicates, were executed by the same analysts over 4 days. Additional controls were included for each monoclonal antibody at the three levels of NaCl content, for example, 0 mM, 50 mM or 100 mM NaCl. Samples were analyzed at two time points (T), such as 15 or 30 minutes, using infectivity assays. The response was X-MuLV LRF at 15 and 30 minutes. JMP® (a statistical software from SAS) was used to perform modeling by least squares estimates. Analysis of variance (ANOVA) was used to identify statistically significant ($P<0.05$) factors and interactions. All non-significant factors ($P>0.05$), collinear factors (VIF>5), and outlier runs (determined by jackknife distances) were removed.

Figure 2B:
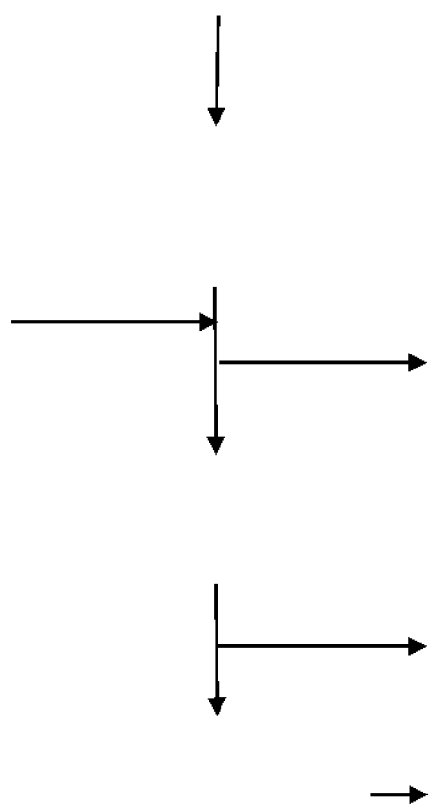
FIG. 2B shows the neutral controls which were performed for each monoclonal antibody salt condition. The purpose of this control is to ensure that the measured viral activity was a result of chemical inactivation at low pH according to an exemplary embodiment.

Neutral controls as shown in FIG. 2B were performed for every monoclonal antibody condition. Neutral controls were performed to ensure that the measured viral activity was a result of chemical inactivation at low pH. The pH of the load material was adjusted to about pH 6.5-7.5. It was expected to observe no clearance in order to demonstrate that virus inactivation did not result from the protein matrix alone. Samples were obtained from the steps of pre-filtration and post-filtration to monitor potential virus loss over the filter. Each condition of a monoclonal antibody had a representative neutral control to serve as the load material for data analysis. The temperature of the environment may influence pH measurement. All virus handling, adjustments and pH measurements occurred at room temperature. Bulk test article was incubated in a water bath at two different temperature conditions. Mettler Toledo Expert Pro were used for measurements.

Example 1. Investigate Factors Having Impacts on Low pH Hold

The impacts of protein type, pH, temperature, acid titrant, NaCl content, spike timing, and post-spike filtration on X-MuLV inactivation for low pH hold were explored through a D-optimal design of experiment as shown in Table 1. The 15 runs with duplicates were performed over 4 consecutive days with the same virus stock, personnel, buffers and equipment. A neutral control was performed for each monoclonal antibody (mAb) condition (mAb type and NaCl content, N=6) and served as the load sample for data analysis. Each run condition and resulting LRF value at both 15 and 30 minute time points is listed in Table 2. Table 2 shows data summary for design of experiment. No virus was detected in 22 of the 30 runs after 30 minutes. The LRF for each of the replicate runs after 30 minutes was within 0.5 LRF of each other, except for 2 runs which were removed as outliers during data analysis. There is no significant day to day or run to run variability in the dataset based on pH measurement, acid addition, or load material.

In table 2, regarding target pH, samples were adjusted to the target pH within a range of ±0.02 pH units. Regarding NaCl content, NaCl was added to bulk material prior to performing titration to low pH using acid. The symbol of ">" denotes that virus was reduced below the limit of detection of the assay. P denotes phosphoric acid. G denotes glycine HCl. Some specific runs were determined as an outlier by jackknife distances and removed prior to further data analysis. Before infectivity assay, sample matrices were evaluated for interference with virus propagation in the indicator cell line, such that a non-interfering dilution could be identified. Based on observed interference, runs were reported at a 3-fold dilution. One replicate run unexpectedly interfered with the infectivity assay at a 3-fold dilution and the reported value was at a 10-fold dilution which prevented interference. This run was determined to be an outlier by jackknife distances and removed from data analysis.

TABLE 2

Data summary for design of experiment

| mAb | Target pH | Temp (° C.) | Acid Titrant | NaCl Content (mM) | Spike Method | Post-spike Filtration | LRF at Each Time Point (min) | |
|---|---|---|---|---|---|---|---|---|
| | | | | | | | 15 | 30 |
| mAb 1 | 3.65 | 20 | G | 0 | 1 | No | >4.06 ± 0.16 | 5.29 ± 0.24 |
| | | | | | | | >4.06 ± 0.16 | 5.38 ± 0.50 |
| | | 15 | P | 50 | 2 | Yes | >4.45 ± 0.26 | >5.90 ± 0.26 |
| | | | | | | | >4.44 ± 0.27 | >5.89 ± 0.27 |
| | | 15 | G | 100 | 1 | No | >4.47 ± 0.13 | >5.92 ± 0.13 |
| | | | | | | | >4.47 ± 0.14 | >5.92 ± 0.14 |
| | 3.73 | 15 | G | 0 | 2 | Yes | >3.06 ± 0.20 | 3.73 ± 0.26 |
| | | | | | | | >3.06 ± 0.21 | 4.29 ± 0.45 |
| | | 20 | P | 100 | 2 | Yes | >4.50 ± 0.09 | >5.95 ± 0.09 |
| | | | | | | | >4.50 ± 0.09 | >5.95 ± 0.09 |
| | 3.80 | 15 | P | 0 | 1 | Yes | 1.92 ± 0.30 | 2.45 ± 0.22 |
| | | | | | | | 1.78 ± 0.31 | 2.55 ± 0.22 |
| | | 20 | G | 50 | 1 | No | 4.47 ± 0.35 | >6.03 ± 0.16 |
| | | | | | | | >4.59 ± 0.16 | >5.92 ± 0.13 |
| | | 15 | P | 100 | 2 | No | >4.47 ± 0.14 | >5.92 ± 0.14 |
| | | | | | | | 3.65 ± 0.39 | >3.47 ± 0.14 |

TABLE 2-continued

Data summary for design of experiment

| mAb | Target pH | Temp (° C.) | Acid Titrant | NaCl Content (mM) | Spike Method | Post-spike Filtration | LRF at Each Time Point (min) | |
|---|---|---|---|---|---|---|---|---|
| | | | | | | | 15 | 30 |
| mAb 2 | 3.65 | 15 | G | 0 | 2 | No | >4.27 ± 0.16 | >5.72 ± 0.16 |
| | | | | | | | 4.14 ± 0.35 | >5.72 ± 0.16 |
| | | 20 | P | 0 | 1 | Yes | >4.19 ± 0.26 | >5.64 ± 0.26 |
| | | | | | | | >4.19 ± 0.26 | >5.64 ± 0.26 |
| | | 20 | G | 100 | 2 | Yes | >4.63 ± 0.15 | >6.08 ± 0.15 |
| | 3.73 | 15 | P | 50 | 1 | No | >4.72 ± 0.06 | >6.16 ± 0.06 |
| | | | | | | | >4.71 ± 0.07 | >6.16 ± 0.07 |
| | 3.80 | 20 | P | 0 | 2 | No | 2.56 ± 0.18 | 2.87 ± 0.19 |
| | | | | | | | 2.48 ± 0.24 | 2.67 ± 0.16 |
| | | 20 | G | 50 | 2 | Yes | >4.49 ± 0.23 | >5.93 ± 0.23 |
| | | | | | | | 4.36 ± 0.39 | >5.93 ± 0.23 |
| | | 15 | G | 100 | 1 | Yes | >4.63 ± 0.16 | >6.08 ± 0.16 |
| | | | | | | | >4.63 ± 0.16 | >6.07 ± 0.16 |

Example 2. Analysis of X-MuLV Inactivation Kinetics at Different Target pH

Figure 3A:
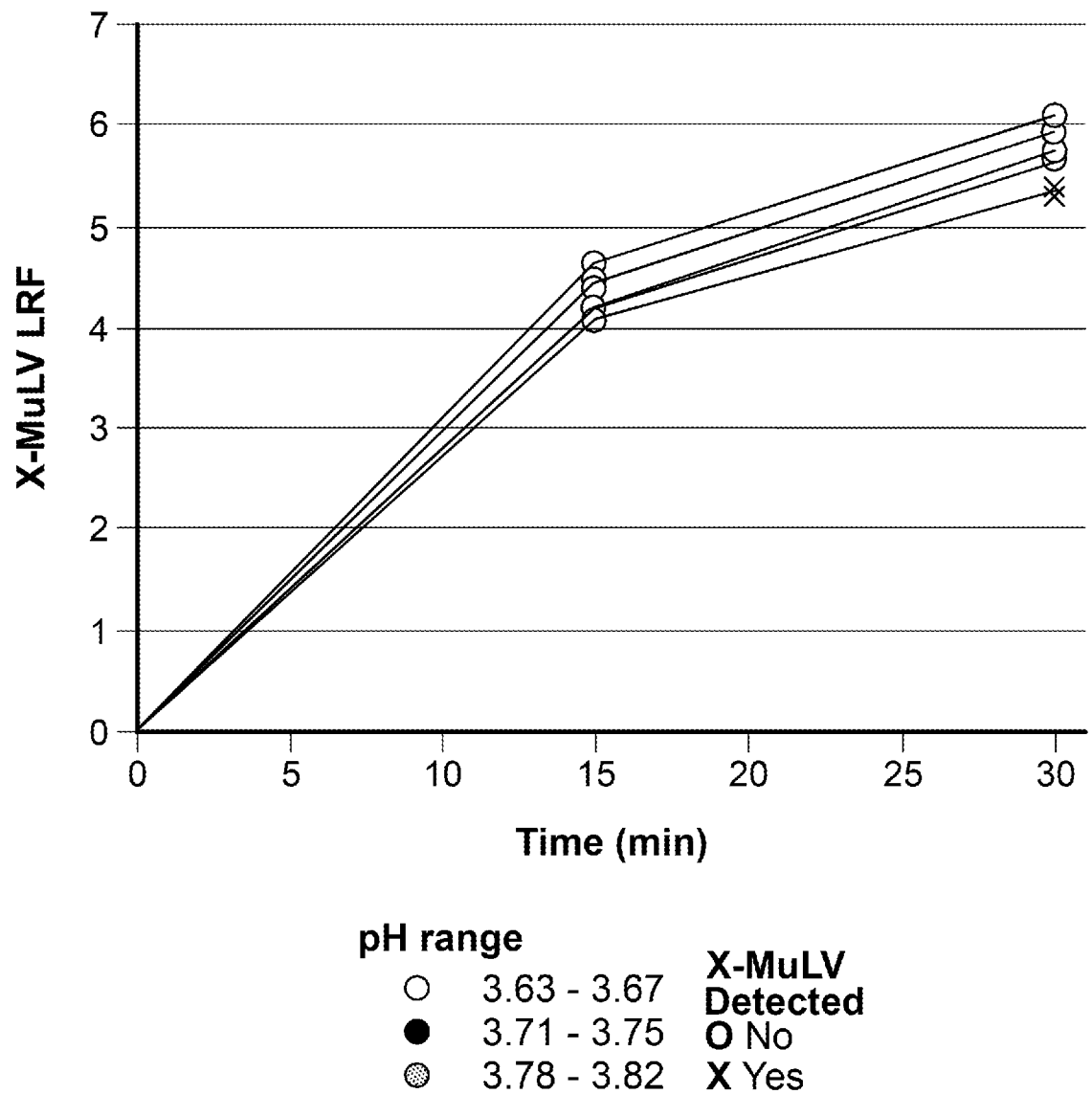
FIG. 3A shows inactivation kinetics of X-MuLV at target pH 3.65 according to an exemplary embodiment. LRF curves at target pH 3.65 were obtained by plotting LRF values against time points according to an exemplary embodiment.
Figure 3B:
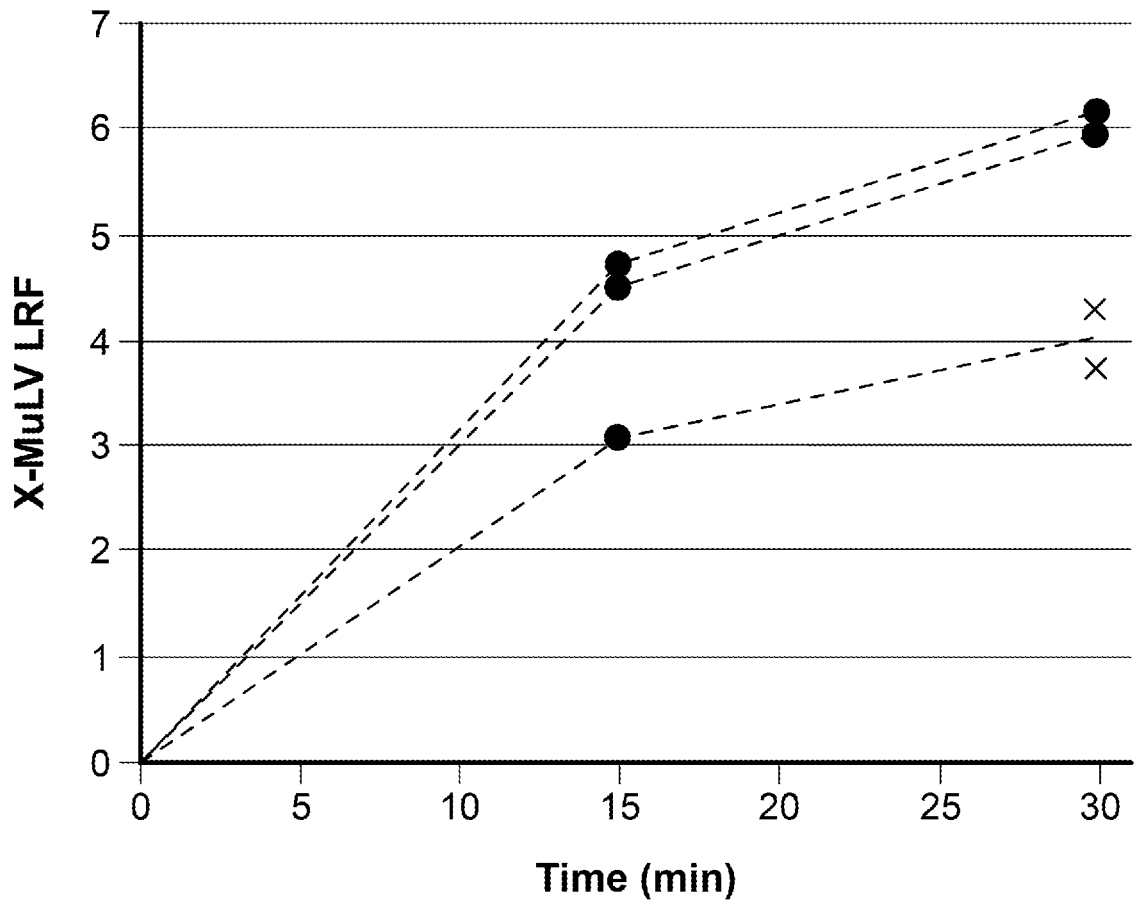
FIG. 3B shows inactivation kinetics of X-MuLV at target pH 3.73 according to an exemplary embodiment. LRF curves at target pH 3.73 were obtained by plotting LRF values against time points according to an exemplary embodiment.
Figure 3C:
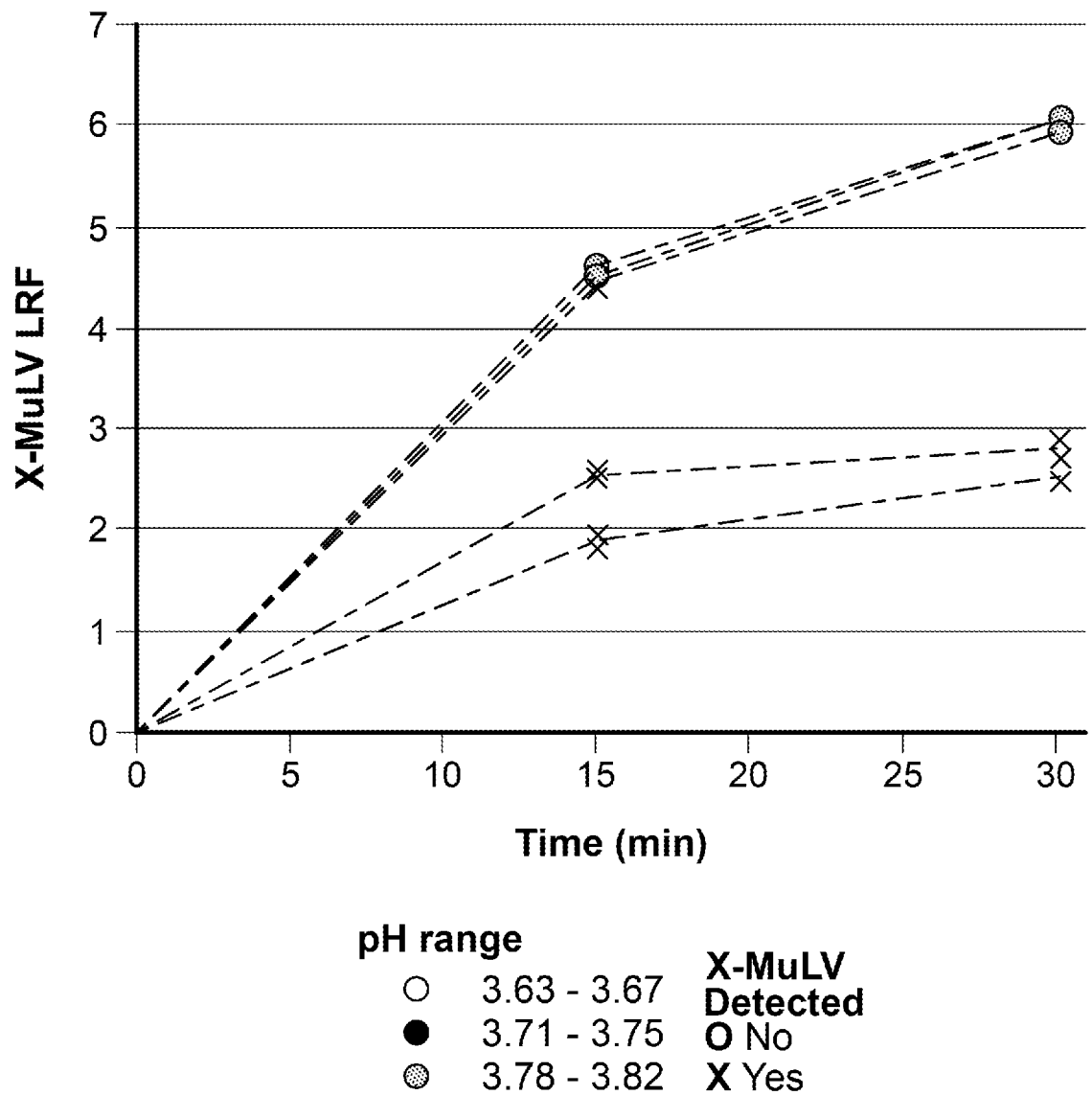
FIG. 3C shows inactivation kinetics of X-MuLV at target pH 3.80 according to an exemplary embodiment. LRF curves at target pH 3.80 were obtained by plotting LRF values against time points according to an exemplary embodiment.

A statistical design of experiment (DoE) was used to evaluate and characterize the effects of a low pH hold step for virus inactivation including the evaluation of several factors, such as protein type, pH condition, temperature, acid titrant, ionic strength of the starting solution, spike timing, and post-spike filtration. The statistical DoE was used to evaluate and characterize the effects of a low pH hold step for virus inactivation. The inactivation kinetics of X-MuLV in view of different target pH were analyzed. Samples at time points of 15 minutes and 30 minutes were tested for X-MuLV infectivity to evaluate the initial inactivation (e.g., 15 minutes) and the inactivation at the end (e.g., 30 minutes) of the low pH hold. FIGS. 3A-3C show inactivation kinetics of X-MuLV at target pH 3.65, pH 3.73 or pH 3.80. LRF curves were obtained by plotting LRF values against time points for each pH value. As shown in FIGS. 3A-3C, open circles denote no virus detected in samples and crosses denote virus detected in samples. Red lines correspond to each run performed at pH 3.65±0.02; green lines correspond to each run performed at pH 3.73±0.02; and blue lines correspond to each run performed at pH 3.80±0.02. As shown in FIG. 3A, for the pH 3.65 runs, no virus was detected in any of the samples at the 15 minute time point, which indicated rapid inactivation of virus (limit of detection approximately 2.5 PFU/mL). At the 30 minute time point for the pH 3.65 runs, 2 runs showed detected virus. However, the results of these two runs were approaching the limit of detection for the assay (approximately 1.0 PFU/mL). At pH 3.65±0.02, all LRFs were greater than 5.0 at 30 minute time point. For the runs of pH 3.73 and pH 3.80, some inconsistencies were present as shown in FIG. 3B and FIG. 3C, since discrepancies occurred between the runs. Some runs at pH 3.73 or pH 3.80 showed similar rapid inactivation as the pH 3.65 runs. One or two runs at pH 3.73 or pH 3.80 showed incomplete inactivation at 30 minutes. The variabilities of these runs suggested that another factor may have a stronger effect than pH conditions.

Figure 4A:
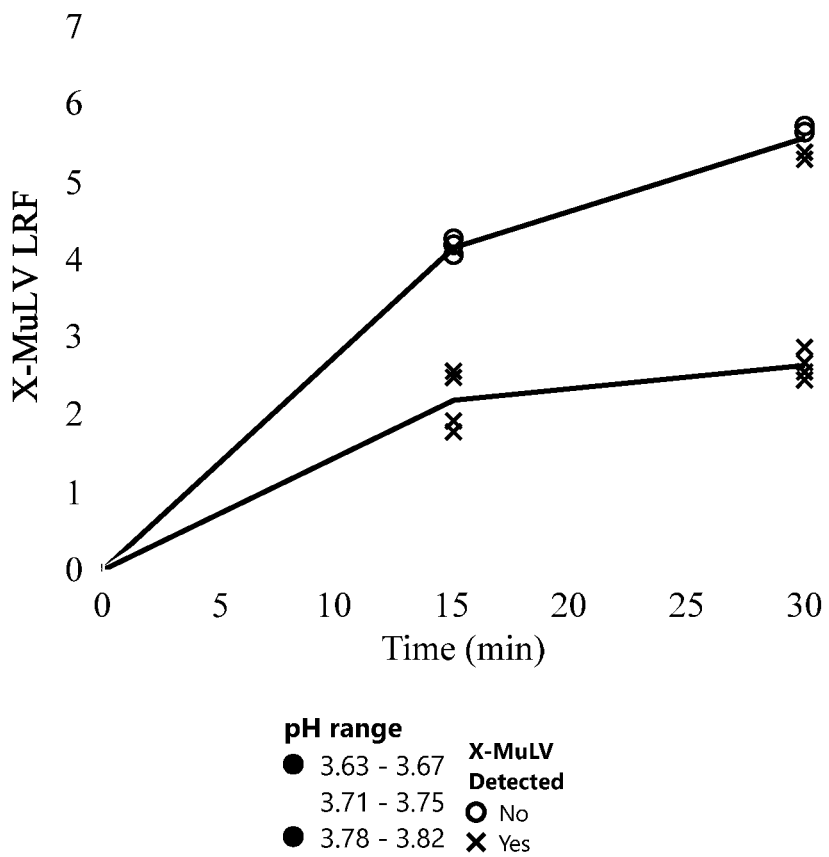
FIG. 4A shows inactivation kinetics of X-MuLV at 0 mM NaCl at different target pH conditions, for example, about pH 3.65, pH 3.73, or pH 3.80, according to an exemplary embodiment. LRF curves were obtained by plotting LRF values against time points for different target pH conditions according to an exemplary embodiment.
Figure 4B:
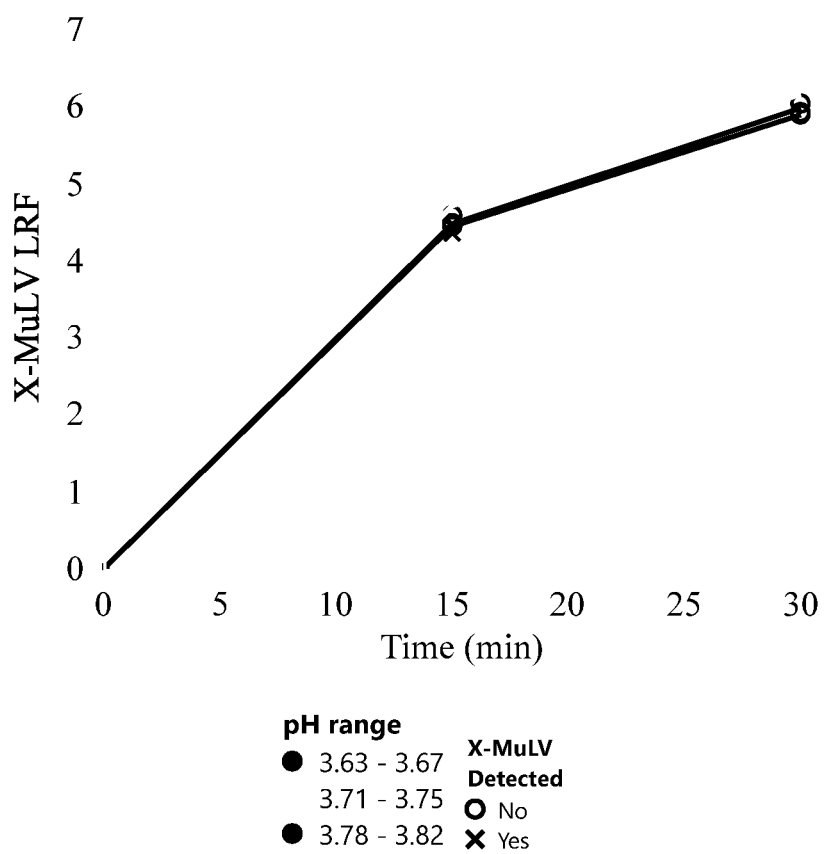
FIG. 4B shows inactivation kinetics of X-MuLV at 50 mM NaCl at different target pH conditions, for example, about pH 3.65, pH 3.73, or pH 3.80, according to an exemplary embodiment. LRF curves were obtained by plotting LRF values against time points for different target pH conditions according to an exemplary embodiment.
Figure 4C:
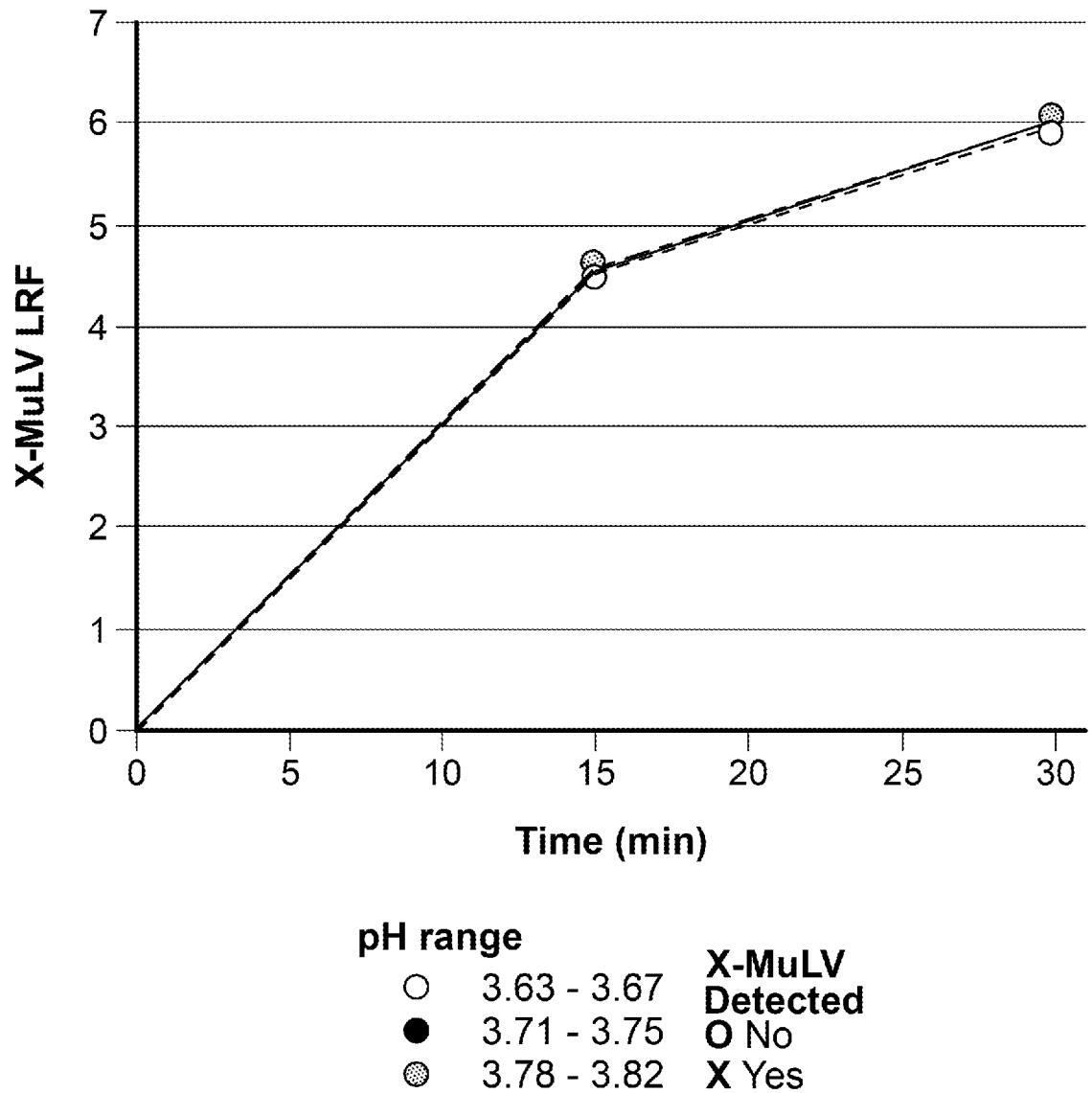
FIG. 4C shows inactivation kinetics of X-MuLV at 100 mM NaCl at different target pH conditions, for example, about pH 3.65, pH 3.73, or pH 3.80, according to an exemplary embodiment. LRF curves were obtained by plotting LRF values against time points for different target pH conditions according to an exemplary embodiment.
Figure 4D:
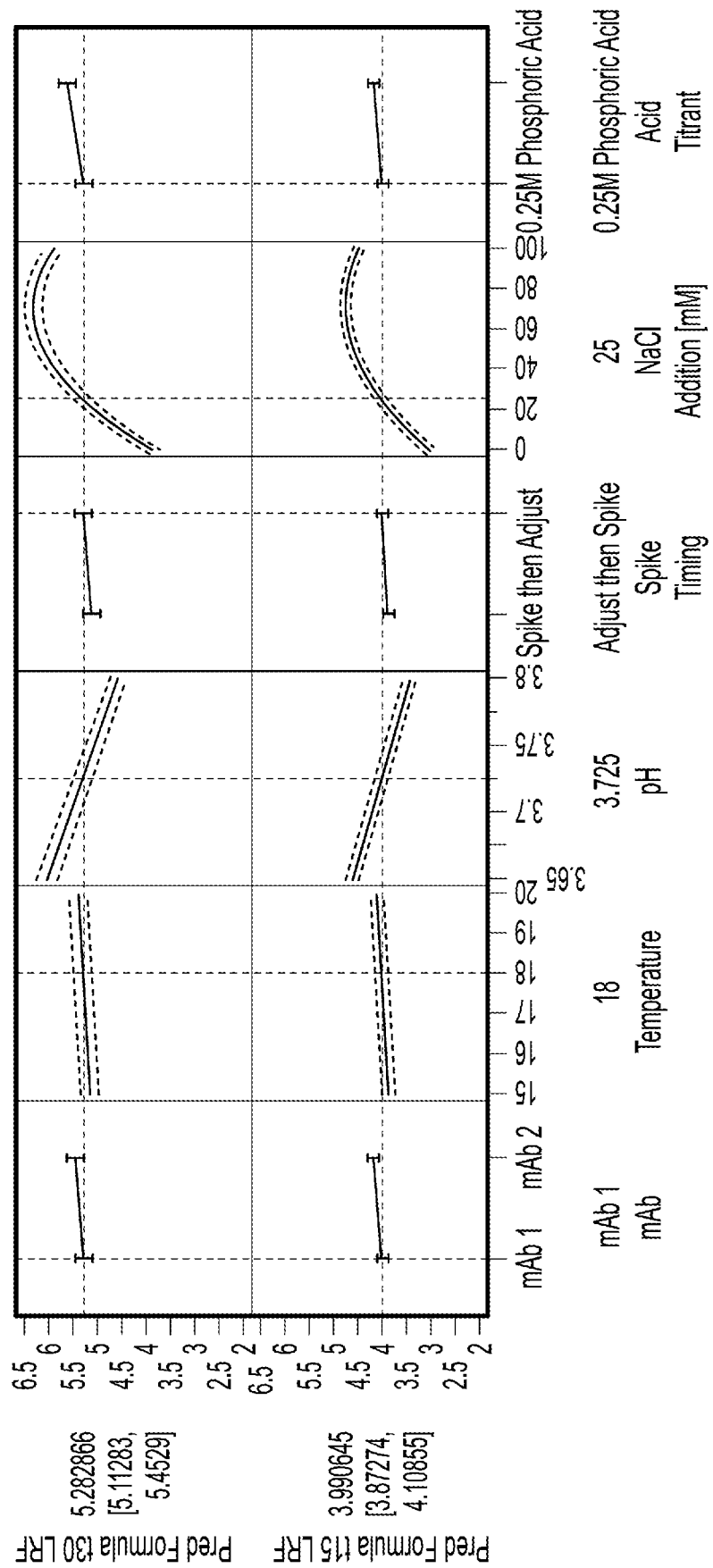
FIG. 4D shows a predicted profiler including parameter estimates to evaluate an operating condition containing about 25 mM NaCl at about pH 3.70-3.75 according to an exemplary embodiment.
Figure 4E:
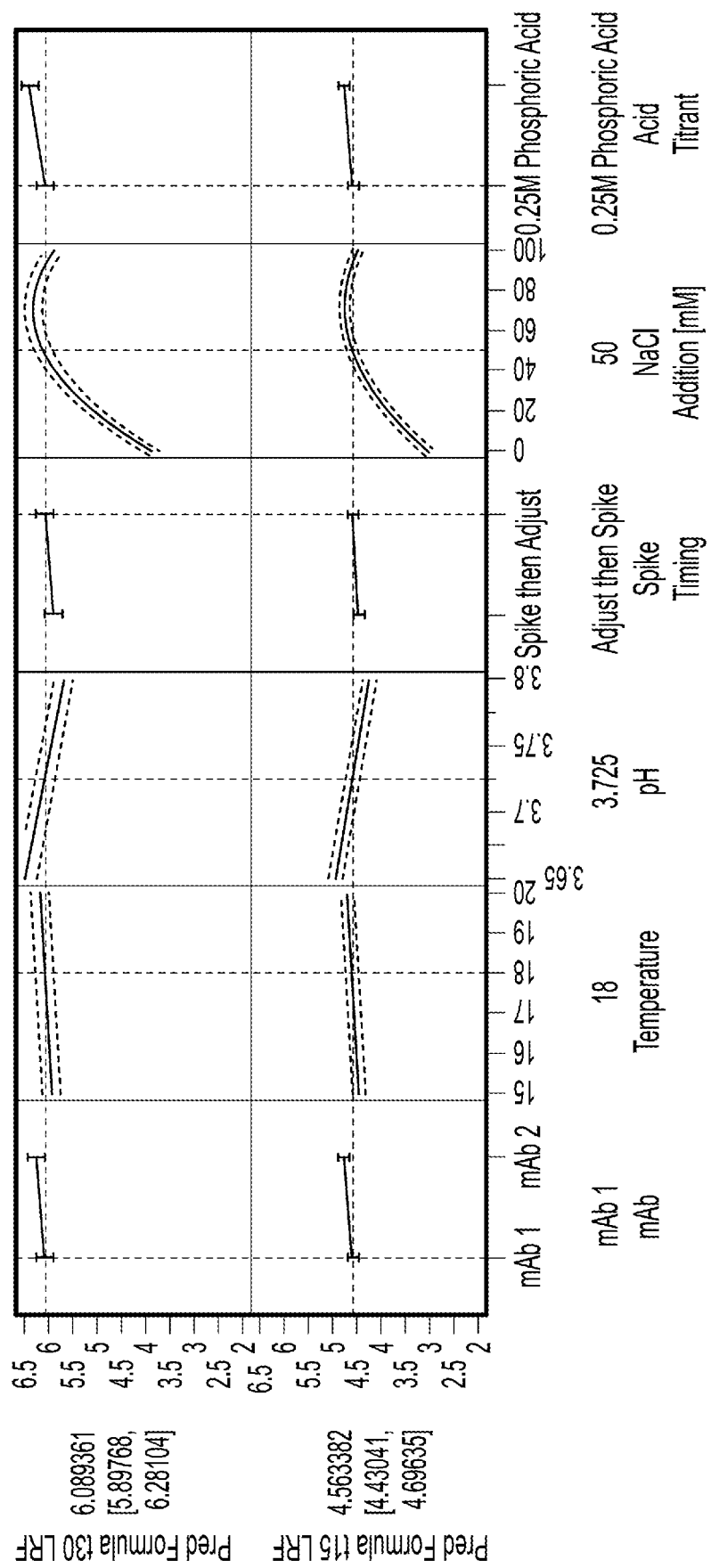
FIG. 4E shows a predicted profiler including parameter estimates to evaluate an operating condition containing about 50 mM NaCl at about pH 3.70-3.75 according to an exemplary embodiment.
Figure 4F:
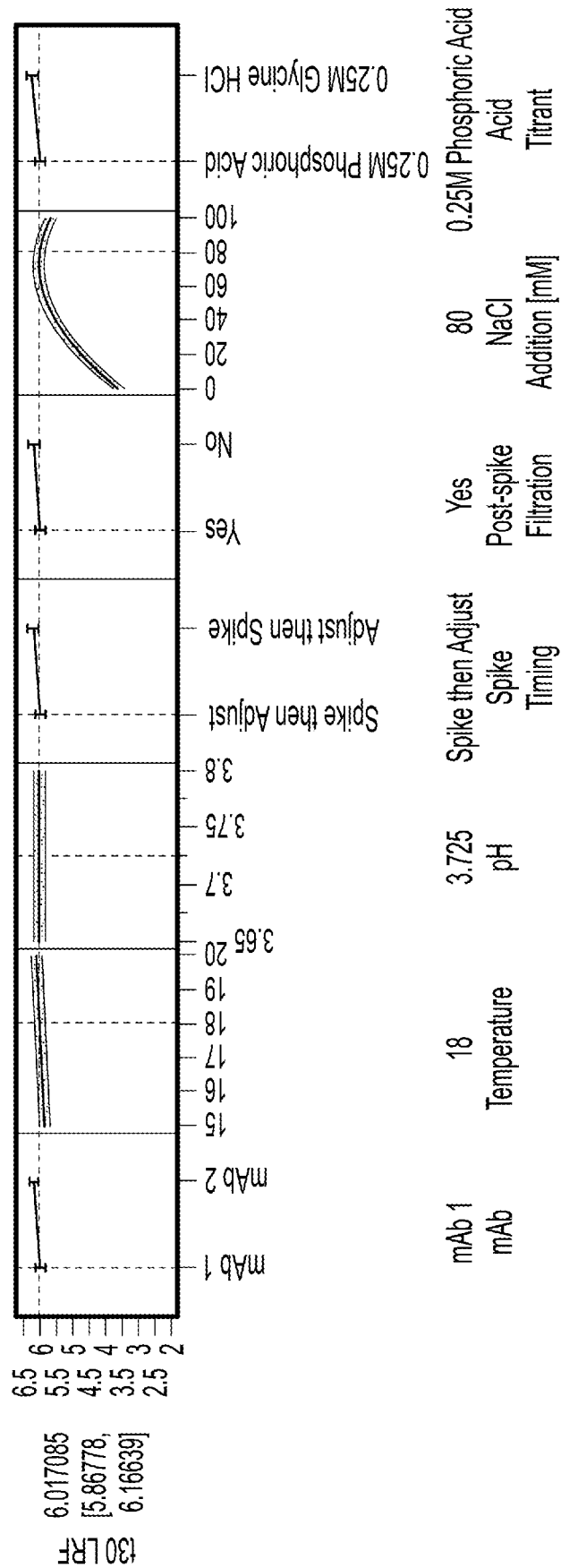
FIG. 4F shows a predicted profiler including parameter estimates to evaluate an operating condition containing about 80 mM NaCl at about pH 3.70-3.75 according to an exemplary embodiment. The effect size of Post-spike filtration was minimal and not included in the overall prediction profiler.

Example 3. Analysis of X-MuLV Inactivation Kinetics at Different NaCl Content More analysis was performed for runs which showed detected retrovirus at the 30 minute time point in Table 2. A common factor, for example, NaCl content, among these runs which had detected virus after 30 minutes was analyzed. The runs were performed without the addition of NaCl in the starting load material. LRF curves were obtained by plotting LRF values against time points for each level of added NaCl. FIGS. 4A-4C show inactivation kinetics of X-MuLV at NaCl content of 0 mM (FIG. 4A), 50 mM (FIG. 4B) or 100 mM (FIG. 4C). As shown in FIGS. 4A-4C, open circles denote no virus detected in samples and crosses denote virus detected in samples. Red lines correspond to each run performed at about pH 3.65±0.02; green lines correspond to each run performed at about pH 3.73±0.02; and blue lines correspond to each run performed at pH 3.80±0.02.

The results showed that conductivity of the starting solution had a strong effect on impacting X-MuLV inactivation kinetics at different target pH conditions. NaCl content was determined to have the largest impact on retrovirus inactivation. The pH condition was an important factor when the load material had low ionic strength or when no additional NaCl was added to the starting material as shown in FIG. 4A. The data suggested that X-MuL V inactivation was dependent on pH at low ionic strength. However, when the ionic strength was increased, for example, increased NaCl concentration, the effects of different target pH conditions were not observed, since X-MuLV was rapidly inactivated at all three target pH conditions. In other words, when the concentration of NaCl increased, the influence of pH conditions on X-MuLV inactivation decreased. When 50 mM or 100 mM NaCl was added, complete and effective clearance of X-MuLV was observed for all runs at 30 minute time points for target pH conditions at pH 3.65, pH 3.73, and pH 3.80 as shown in FIG. 4B (50 mM NaCl) or FIG. 4C (100 mM NaCl), respectively. At low conductivity (e.g., low NaCl content), pH has a strong effect on X-MuLV inactivation. At higher conductivity (e.g., higher NaCl content), pH has no effect on X-MuLV inactivation. 0.25 M glycine HCl showed increased X-MuLV inactivation in comparing to 0.25 M phosphoric acid.

Example 4. Generation of Multivariate Linear Regression Models

Figure 5A:
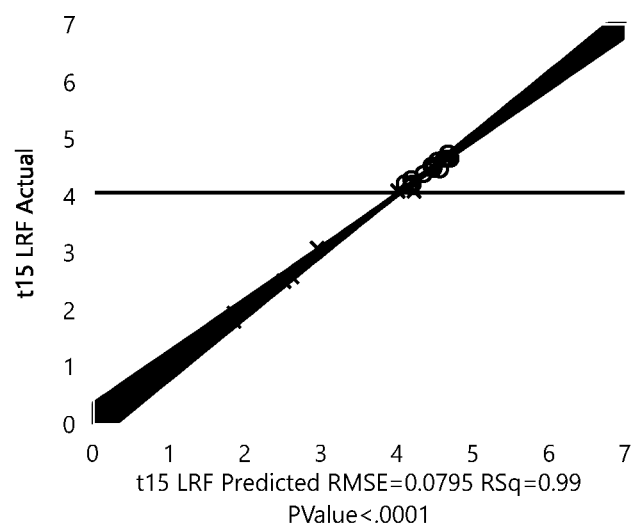
FIG. 5A shows actual versus predicted values of the multivariate linear regression models for LRF for 15 minute time points according to an exemplary embodiment.
Figure 5B:
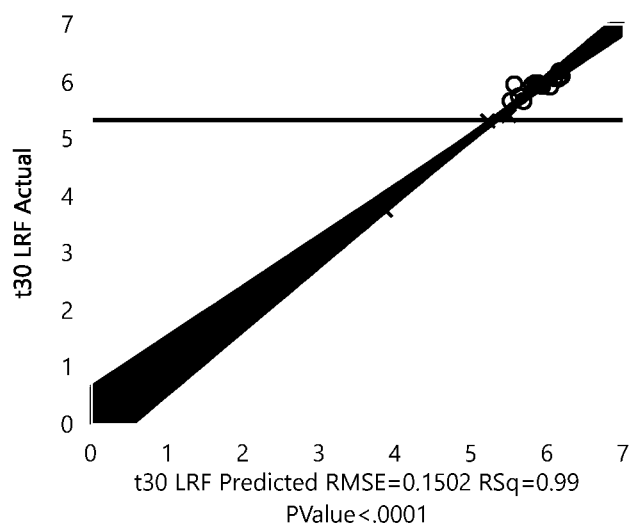
FIG. 5B shows actual versus predicted values of the multivariate linear regression models for LRF for 30 minute time points according to an exemplary embodiment.

In order to investigate the impacts of different factors, a multivariate linear regression model was generated to investigate the main effects, quadratics, and interactions of the factors evaluated. In addition, the effects of ionic strength on X-MuLV inactivation at both 15 and 30 minute time points were quantified. The models generated had adjusted R2 values of about 99% including an estimate of error of <0.15 LRF as shown in Table 3, whereas the reported variability of the infectivity assay is 0.5 LRF (ICH Q5A (R1)). In table 3, R2 denotes correlation coefficient; adjusted R2 denotes amount of variation explained by the model; and RMSE denotes root mean square error for the estimate of the error in the method. Table 4 shows a list of significant (P<0.05) factors for each model. Actual versus predicted plots are shown in FIG. 5A and FIG. 5B. The plots for actual versus predicted values of the multivariate linear regression models for LRF for two time points were shown in FIG. 5A and FIG. 5B, e.g., 15 minutes (FIG. 5A) or 30 minutes (FIG. 5B). Red line denotes fit line, blue line denotes mean line, and red shaded line denotes 95% confidence interval in FIG. 5A and FIG. 5B.

TABLE 3

Significant multivariate linear regression model fit for each time point

| Time Point (min) | $R^2$ | Adjusted $R^2$ | RMSE (LRF) |
|---|---|---|---|
| 15 | 0.99 | 0.99 | 0.08 |
| 30 | 0.99 | 0.99 | 0.15 |

TABLE 4

Significant factors determined from generated LRF multivariate linear regression model for each time point

| | LRF at 15 minutes | | LRF at 30 minutes | |
|---|---|---|---|---|
| Factor | Prob > \|t\| | Effect Size | Prob > \|t\| | Effect Size |
| [NaCl] | <0.0001 | 1.51 | <0.0001 | 2.10 |
| [NaCl] * [NaCl] | <0.0001 | 0.79 | <0.0001 | 1.18 |
| pH | <0.0001 | 0.69 | <0.0001 | 1.01 |
| pH * [NaCl] | <0.0001 | 0.45 | <0.0001 | 0.65 |
| Temperature | <0.0001 | 0.25 | 0.0003 | 0.27 |
| mAb | <0.0001 | 0.19 | 0.0070 | 0.18 |
| mAb * pH | — | — | 0.0021 | 0.11 |
| Post-spike Filter | <0.0001 | 0.19 | 0.0136 | 0.17 |
| Titrant | 0.0017 | 0.12 | 0.0015 | 0.24 |
| Spike Method | 0.0138 | 0.09 | 0.0044 | 0.20 |

The significant parameters for the LRF model generated for 15 and 30 minutes were the same, showing similar trends in effect size. However, the interaction between mAb and pH was exceptional, since it was significant for only the 30 minute LRF model. The pH conditions were known to be important for virus inactivation. However, the model indicated that NaCl showed the strongest effect on X-MuLV inactivation at both 15 and 30 minute time points. When the NaCl concentration was increased, the LRF of X-MuLV increased accordingly until the ionic strength had no impact on inactivation. Other factors which were determined to be important were the quadratic of NaCl content, the interaction between pH and NaCl content, and pH conditions. The effect of NaCl concentration on inactivation kinetics can be explained according to FIG. 6. When NaCl concentration was increased, the influence of pH on X-MuLV inactivation decreased.

The main effect of temperature, mAb, post-spike filtration, acid titrant, spike method, and the interaction between pH and mAb were all significant within the linear regression model. However, the effect size of these factors was less than the reported infectivity assay variability (e.g., 0.5 LRF). Although these factors were significant (P<0.05) within the generated model, they were not practically significant as the effect size was less than the infectivity assay variability. Temperature had a known effect on virus inactivation, since lower temperature correlated with reduced inactivation kinetics. However, this data set supported a minimal difference in inactivation due to the operation between the ranges of 15° C. and 20° C.

Figure 6:
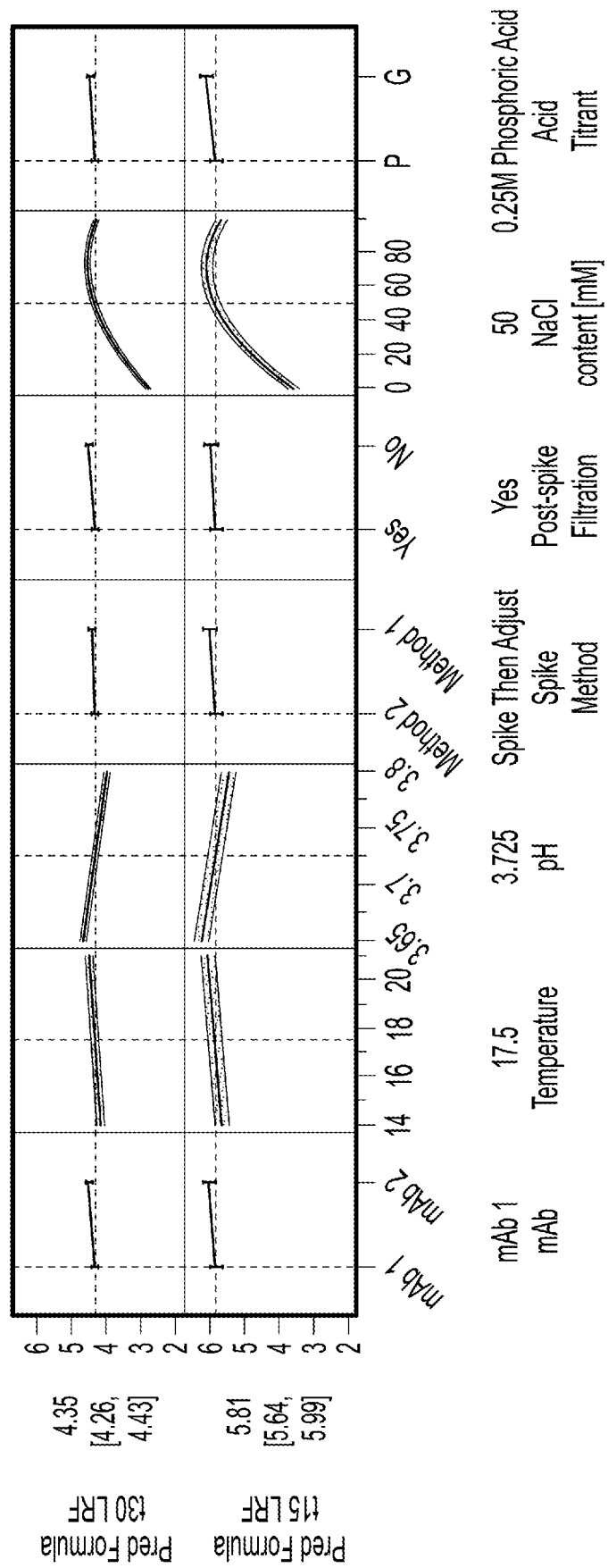
FIG. 6 shows a prediction profiler which was created to optimize the model to achieve greater than 4 LRF after both 15 and 30 minute time points according to an exemplary embodiment. The prediction profiler represented X-MuLV inactivation as a function of the significant factors evaluated in the D-optimal DoE according to an exemplary embodiment.

A prediction profiler was created to optimize the model to achieve greater than 4 LRF after both 15 and 30 minute time points as shown in FIG. 6. FIG. 6 shows a prediction profiler representing X-MuLV inactivation as a function of the significant factors evaluated in the D-optimal DoE: red line denotes fit line; blue line denotes mean line; red shaded line denotes 95% confidence interval; P denotes phosphoric acid; and G denotes glycine HCl. With all other factors remaining constant, an increase in conductivity through the addition of NaCl at operating viral inactivation in the range of about pH 3.60 to 3.90 can result in greater retrovirus LRFs.

The testing results of the statistical DoE for low pH hold in the present application were consistent with the ASTM standard for 5.0 LRF X-MuLV inactivation at pH less than 3.60. The results also demonstrated robust and effective inactivation at pH greater than 3.60. For ranges outside the ASTM generic claim, the results indicated that increasing the NaCl content can achieve rapid and effective X-MuLV inactivation. Typically, the pH of the hold is dependent on the stability of the protein. The models of the present application can be used to predict effective clearance when operating viral inactivation in the range of pH 3.60-3.90 by manipulating conductivity of the low pH starting material.

High protein concentration, such as greater than 25 g/L, has been reported to negatively impact X-MuLV inactivation (ASTM). However, previous Regeneron studies have demonstrated that higher protein concentration can potentially improve X-MuLV inactivation kinetics under conditions where inactivation may not be complete. Conditions with increased ionic strength, such as higher buffer concentration, titration of a weak acid or higher protein concentration correlated with higher LRFs at higher pH (Chinniah et al.). Although the dataset of the present application used two monoclonal antibodies having similar concentrations, the conclusions from the data agreed with the conclusion that an increase in protein concentration would increase inactivation. More ions were added during titration due to the increase in acid titrant which was required to achieve the desired pH. The result was an increase in the ionic strength of the solution and this experiment would suggest greater inactivation kinetics.

Similar to the impact of protein concentration, there was a significant difference observed by the model for acid titrant, where the glycine HCl acid titrant (weaker acid) was correlated with higher LRF values of the phosphoric acid titrant (stronger acid). This conclusion was not practically significant because the effect size was less than 0.5 LRF. The results supported increasing inactivation due to increasing ion concentration in solution. Previous studies showed lower clearance at lower temperatures dues to the thermodynamics of virus inactivation. Temperature was statistically significant in the generated linear regression model, but had a minimal effect size within the studied range (15 to 20° C.). Previous studies conclude that there is no statistically significant difference on virus inactivation between 15° C. and 16+° C. (Mattila et al., Retrospective evaluation of low-pH virus inactivation and viral filtration data from a multiple company collaboration, PDA Journal of Pharmaceutical Science and Technology 70.3 (2016): 293-299). The experiment of the present application supported the ASTM generic viral clearance claim as well as identifying a solution to achieve effective inactivation of retrovirus at greater than pH 3.60. At higher pH, increasing the ionic strength of the solution can promote virus dispersion. In low conductivity solutions, retroviral glycoproteins can potentially aggregate at low pH and protect themselves from chemical damage. With the addition of 50 mM and 100 mM NaCl, all runs at all pH set points showed complete and effective clearance after 30 minutes. In summary, an operating space can be defined for effective X-MuLV inactivation, when the experiment is operated at a pH which is outside of the ASTM modular claim.

Example 5. Evaluate Existing and Redesigned Operating Conditions

Figure 7:
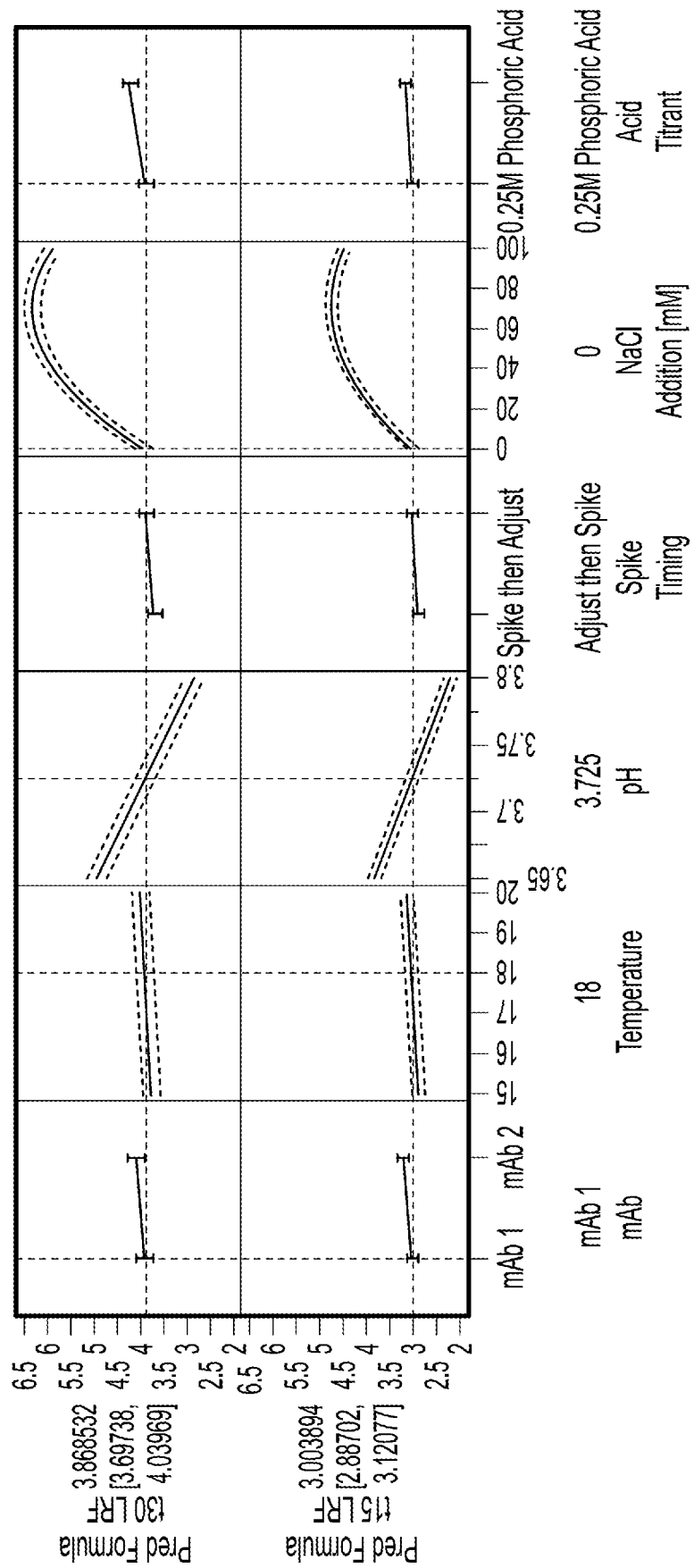
FIG. 7 shows predicted profilers including parameter estimates for some existing operating conditions at about pH 3.70-3.75 for low pH hold according to an exemplary embodiment. The effect size of Post-spike filtration was minimal and not included in the overall prediction profiler.

A statistical design of experiment (DoE) was used to evaluate and characterize the effects of a low pH hold step for virus inactivation including the evaluation of several factors, such as protein type, pH condition, temperature, acid titrant, NaCl content, spike timing, and post-spike filtration. The DoE for the low pH hold step was used to evaluate some existing operating conditions at pH 3.70-3.75 for low pH hold. Predicted profilers including parameter estimates were generated as shown in FIG. 7.

Figure 8:
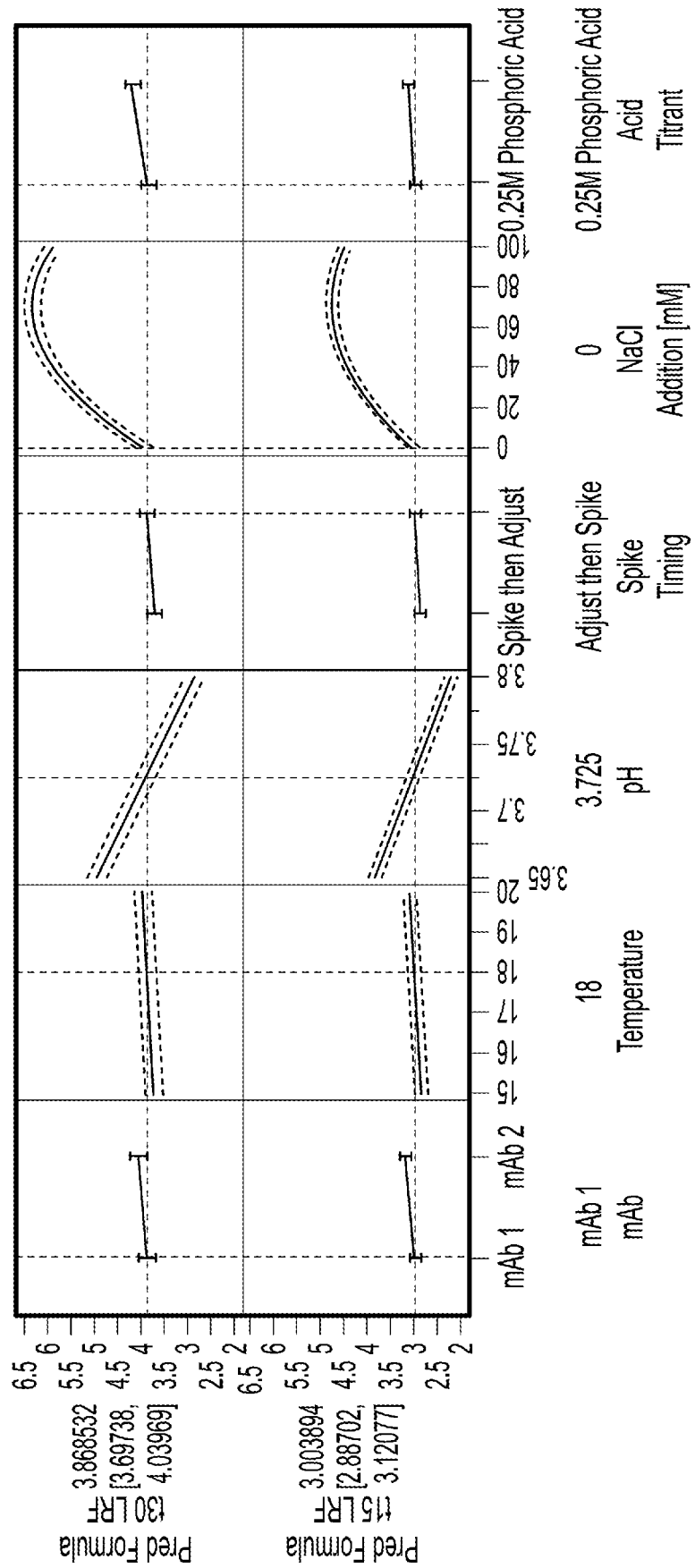
FIG. 8 shows predicted profilers including parameter estimates for redesigned operating conditions at about pH 3.65-3.70 for low pH hold according to an exemplary embodiment. The effect size of Post-spike filtration was minimal and not included in the overall prediction profiler.

The DoE for the low pH hold step was also used to evaluate some existing redesigned operating conditions at pH 3.65-3.70 for low pH hold. Predicted profilers including parameter estimates were generated as shown in FIG. 8. The redesigned operating conditions at about pH 3.65-3.70 failed to satisfy 4 LRF X-MuLV clearance at 30 minute time points at the 1.5% failure rate.

Example 6. Evaluate the Factor of Protein Types

Figure 9:
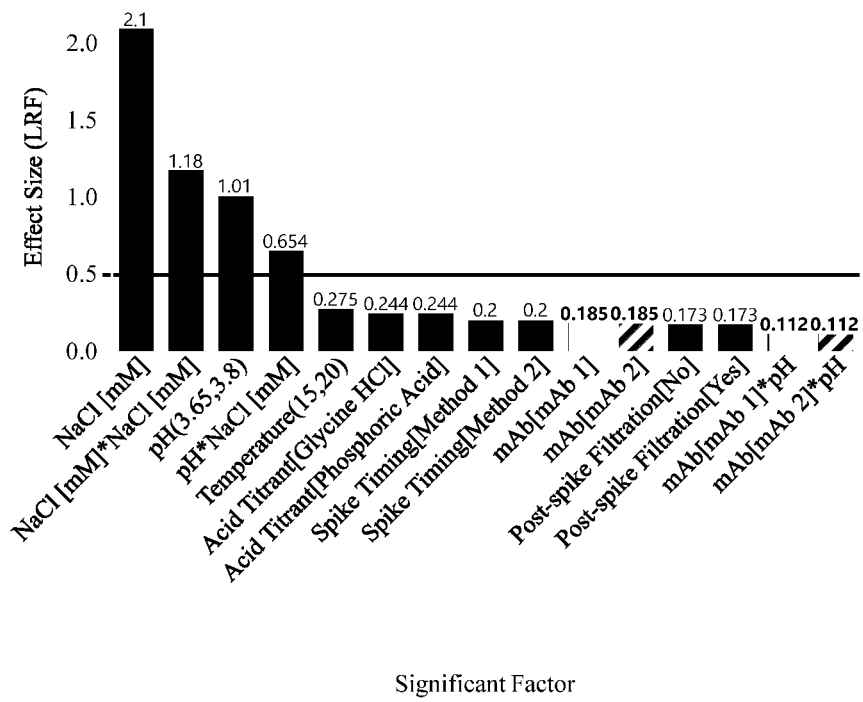
FIG. 9 shows effect size for evaluated factors, including NaCl, pH, acid titrant, temperature, protein type (mAb, monoclonal antibody), spike timing and combinations thereof and X-MuLV LRF at 30 minute time point for protein types including IgG1 and IgG2 based on retrospective data according to an exemplary embodiment.

The statistical DoE was used to evaluate and characterize the effects of a low pH hold step for virus (X-MuLV) inactivation including the evaluation of several factors, such as protein type, pH condition, temperature, acid titrant, NaCl content, spike timing, and post-spike filtration. The DoE showed statistical significance in the predictions of the multivariate models for protein types, such as the isotypes of monoclonal antibodies, but the differences between protein types, such as IgG 1 and IgG4, were not meaningful in the study ranges as shown in FIG. 9. FIG. 9 shows scaled estimated LRF for evaluated factors, including NaCl, pH, acid titrant, temperature, protein type (mAb, monoclonal antibody), spike timing and combinations thereof. The retrospective data for existing operating conditions showed significant differences between isotypes of monoclonal antibodies, such as IgG1 and IgG4. However, these differences could be due to the differences in operating pH ranges. FIG. 9 also shows X-MuLV LRF at 30 minute time point for protein types including IgG1 and IgG2 based on retrospective data.

Example 7. Evaluate the Factor of Temperature

Figure 10:
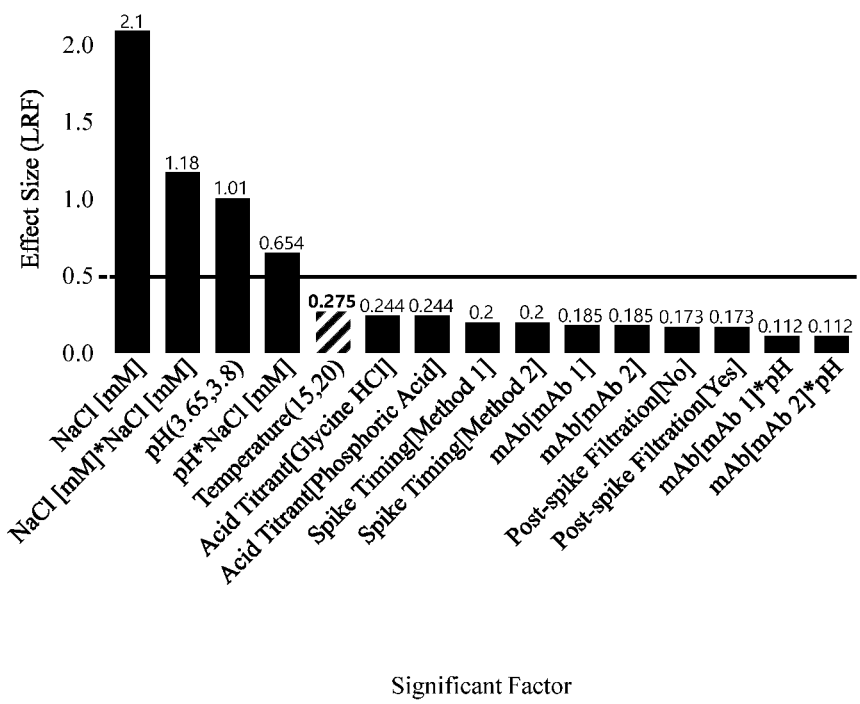
FIG. 10 shows effect size for evaluated factors, including NaCl, pH, acid titrant, temperature, protein type (mAb, monoclonal antibody), spike timing and combinations thereof and retrovirus LRF for different temperature conditions based on retrospective industrial data according to an exemplary embodiment.

The statistical DoE was used to evaluate and characterize the effects of a low pH hold step for virus (X-MuLV) inactivation including the evaluation of several factors, such as protein type, pH condition, temperature, acid titrant, NaCl content, spike timing, and post-spike filtration. The DoE showed statistical significance in the predictions of the multivariate models for temperature, but the differences between different temperature conditions have minimal effects on X-MuLV clearance in the study ranges as shown in FIG. 10. FIG. 10 shows scaled estimated LRF for evaluated factors, including NaCl, pH, acid titrant, temperature, protein type (mAb, monoclonal antibody), spike timing and combinations thereof. The retrospective data from industrial operating conditions (Mattila et al.) in the range of from 15° C. to 20° C. showed no statistically significant differences between 15±1° C. and 16+° ° C. FIG. 10 also shows retrovirus LRF for different temperature conditions based on retrospective industrial data.

Example 8. Evaluate the Factor of Spike Timing

The statistical DoE was used to evaluate and characterize the effects of a low pH hold step for virus (X-MuLV) inactivation including the evaluation of several factors, such as protein type, pH condition, temperature, acid titrant, NaCl content, spike timing, and post-spike filtration. The spiking timing in the statistically DoE of the present application is an adjust-spike-readjust method or a spike-adjust method. Under the adjust-spike-readjust method, samples are adjusted/titrated to the target pH then spiked with the virus stock having pH 7.2. Timing of the pH hold began at the time of spiking. Due to the observation of pH increases after spiking virus stock, the pH of the samples were readjusted to the target pH prior to being held at the desired temperature for the remainder of the pH hold. Under the spike-adjust method, samples are first spiked with the virus stock solution then adjusted/titrated to the target pH. When the target pH is reached, timing of the pH hold started, and the sample is incubated at the desired temperature.

Figure 11:
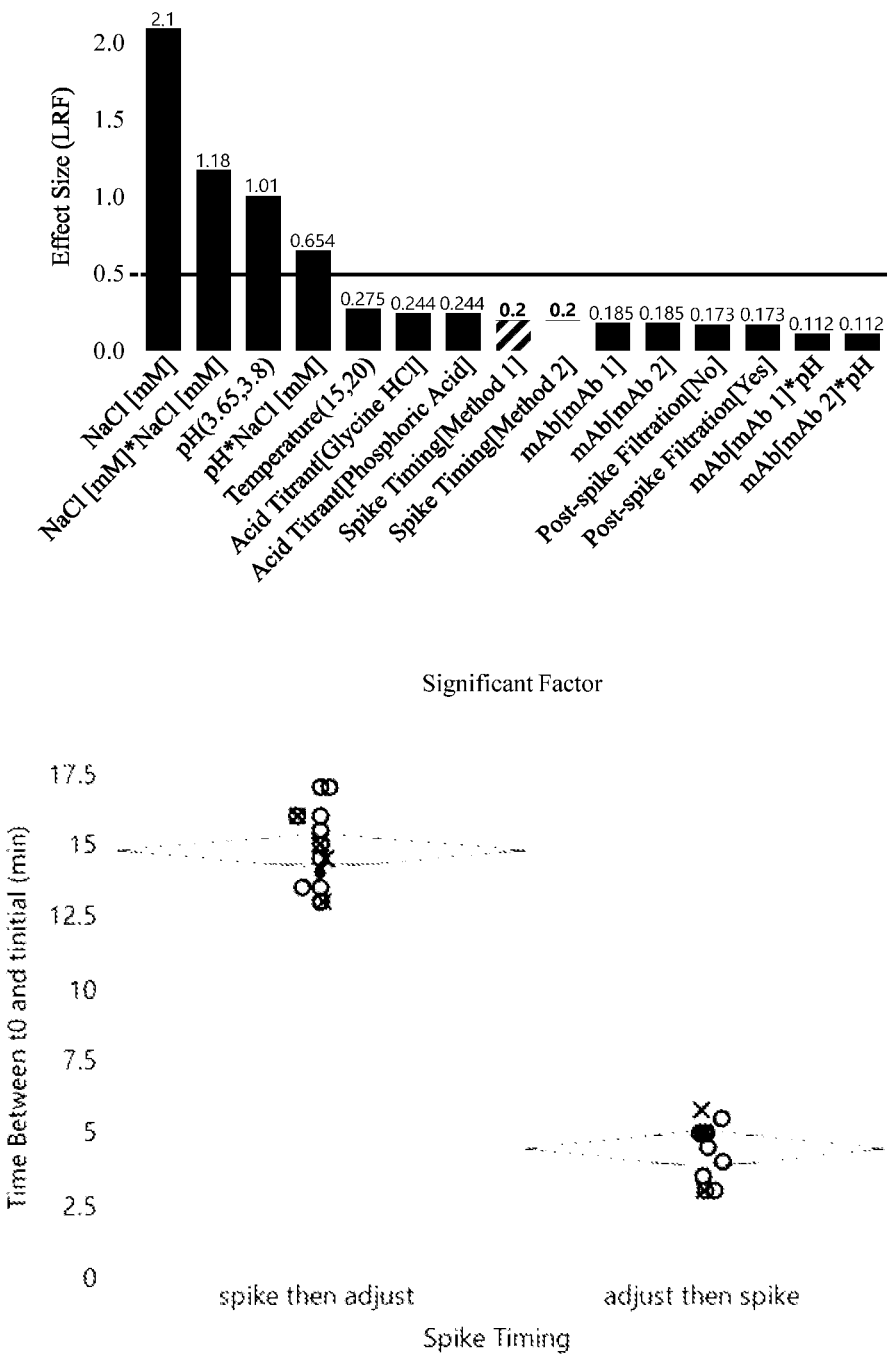
FIG. 11 shows effect size for evaluated factors, including NaCl, pH, acid titrant, temperature, protein type (mAb, monoclonal antibody), spike timing and combinations thereof and the time for spiking/adjusting for two methods according to an exemplary embodiment.

The differences in spike timing for two different methods have no meaningful differences on X-MuLV clearance in the study ranges as shown in FIG. 11. FIG. 11 shows scaled estimated LRF for evaluated factors, including NaCl, pH, acid titrant, temperature, protein type (mAb, monoclonal antibody), spike timing and combinations thereof. FIG. 11 also shows the time for spiking/adjusting for two methods.

What is claimed is:

1. A method for purifying a peptide or protein from a sample, the method comprising:
    subjecting the sample to increasing ionic strength by addition of sodium chloride, wherein the concentration of the sodium chloride is from about 1 mM to about 100 mM;
    subjecting the sample to an acidic pH, and
    subsequently maintaining the sample at the ionic strength condition and the pH condition for at least about 15 minutes to inactivate a quantity of viral particles;
    wherein the sample comprises one or more impurities including the viral particles.

2. The method of claim 1, wherein the quantity of the viral particle inactivation is at least about 3 LRF (logarithmic reduction factor).

3. The method of claim 1, wherein the quantity of the viral particle inactivation is at least about 4 LRF.

4. The method of claim 1, wherein the pH condition of the sample is less than or equal to about pH 3.90.

5. The method of claim 1, wherein the pH condition of the sample is in a range of from about pH 3.60 to about pH 3.90.

6. The method of claim 1, wherein the pH condition of the sample is in a range of from about pH 3.65 to about pH 3.80.

7. The method of claim 1, wherein the peptide or protein is an antibody produced in a host cell.

8. The method of claim 1, wherein the sample is maintained at the ionic strength condition and the pH condition for at least about 30 minutes to inactivate the quantity of the viral particles.

9. The method of claim 1, wherein the sample is maintained at the ionic strength condition and the pH condition for from about 15 minutes to about 30 minutes to inactivate the quantity of the viral particles.

10. The method of claim 1 further comprising optimizing the ionic strength and the pH condition of the sample for inactivation of the quantity of the viral particles by running a D-Optimal design of experiment.

11. The method of claim 10, wherein the D-Optimal design of experiment evaluates the pH condition of the sample and the ionic strength of the sample and adjusts the pH condition of the sample and the ionic strength of the sample to inactivate a quantity of viral particles.

12. The method of claim 11, wherein the D-Optimal design of experiment further evaluates and adjusts one or more of:
 a conductivity of the sample;
 a type of the peptide or protein;
 a temperature of the sample;
 an acid titrant to adjust the pH condition of the sample;
 a method for spiking the viral particles to the sample; or
 a presence of a post-spike filtration.

13. The method of claim 1, wherein the sample is an eluent from protein A chromatography.

14. The method of claim 1, wherein the ionic strength of the sample is adjusted using an addition of sodium chloride, wherein a concentration of the sodium chloride is in a range of from about 1 mM to about 100 mM, or is about 25 mM, about 50 mM or about 100 mM.

15. The method of claim 1, wherein the concentration of the sodium chloride is in a range of from about 1 mM to about 50 mM.

16. The method of claim 1, wherein the concentration of the sodium chloride is about 25 mM, about 50 mM, or about 100 mM.

17. The method of claim 1, wherein the pH condition of the sample is adjusted using phosphoric acid or glycine HCl.

18. The method of claim 1, wherein the peptide or protein is an antibody having an IgG1 isotype or having an IgG4 isotype.

19. The method of claim 1, wherein the peptide or protein is a monoclonal antibody or a bispecific antibody.

20. The method of claim 1, wherein the peptide or protein is an antibody, an antibody fragment, a Fab region of an antibody, an antibody-drug conjugate, a fusion protein, a protein pharmaceutical product or a drug.

21. A method of producing a preparation comprising a protein of interest and a reduced amount of viral particles from a sample having the protein of interest and an viral particle, comprising:
 subjecting the sample to a pH of greater than about 3.6;
 subjecting the sample to an increase in ionic strength condition by addition of sodium chloride to the starting solution, wherein the concentration of sodium chloride is from about 1 mM to about 100 mM; and
 maintaining the sample at the pH and ionic strength condition for an appropriate amount of time to produce the preparation comprising the protein of interest and the reduced amount of viral particles.

22. The method of claim 21, wherein the concentration of the protein of interest in the sample is greater than about 25 g/L.

23. The method of claim 21, wherein the appropriate amount of time is about 15 minutes, about 20 minutes, about 25 minutes, or about 30 minutes.

24. The method of claim 21, wherein the method reduces the amount of infectious viral particles from a sample by about 3 LRF (logarithmic reduction factor).

25. The method of claim 21, wherein the method reduces the amount of infectious viral particles from a sample by about 4 LRF (logarithmic reduction factor).

26. The method of claim 21, wherein the pH condition of the sample is greater than about pH 3.70, about 3.80, about pH 3.90 or about pH 4.0.

27. The method of claim 21, wherein the pH condition of the sample is in a range of from about pH 3.60 to about pH 4.0.

28. The method of claim 21, wherein the sample is an eluent from protein A chromatography.

29. The method of claim 21, wherein the ionic strength of the sample is adjusted using an addition of sodium chloride, wherein a concentration of the sodium chloride is in a range of from about 1 mM to about 200 mM.

30. The method of claim 21, wherein the concentration of the salt is greater than about 50 mM, or about 100 mM.

31. The method of claim 21, wherein the pH condition of the sample is adjusted using phosphoric acid or glycine HCl.

32. A method for purifying a peptide or protein from a sample containing IgG1 or IgG4, the method comprising:
 subjecting the sample to increasing ionic strength by addition of a salt, wherein the concentration of the salt is from about 1 mM to about 100 mM;
 subjecting the sample to an acidic pH, and
 subsequently maintaining the sample at the ionic strength condition and the pH condition for at least about 15 minutes to inactivate a quantity of viral particles;
 wherein the sample comprises one or more impurities including the viral particles.

33. The method of claim 32 further comprising optimizing the ionic strength and the pH condition of the sample for inactivation of the quantity of the viral particles by running a D-Optimal design of experiment.

34. The method of claim 33, wherein the D-Optimal design of experiment evaluates the pH condition of the sample and the ionic strength of the sample and adjusts the pH condition of the sample and the ionic strength of the sample to inactivate a quantity of viral particles.

35. The method of claim 34, wherein the D-Optimal design of experiment further evaluates and adjusts one or more of:
 a conductivity of the sample;
 a type of the peptide or protein;
 a temperature of the sample;
 an acid titrant to adjust the pH condition of the sample;
 a method for spiking the viral particles to the sample; or
 a presence of a post-spike filtration.

36. The method of claim 32, wherein the pH condition of the sample is adjusted using phosphoric acid or glycine HCl.

37. The method of claim 1, wherein
 the pH condition of the sample is in a range of from about pH 3.60 to about pH 3.90;
 the concentration of the sodium chloride is about 25 mM, about 50 mM, or about 100 mM;
 the sample is subjected to an acidic pH by a concentration of phosphoric acid or glycine HCl of about 0.25 M; and
 the quantity of the viral particle inactivation is at least about 3 LRF (logarithmic reduction factor).

38. The method of claim 21, wherein
the pH condition of the sample is in a range of from about pH 3.60 to about pH 3.90;
the concentration of the sodium chloride is about 25 mM, about 50 mM, or about 100 mM;
the sample is subjected to a pH of about 3.6 to 3.9 by a concentration of phosphoric acid or glycine HCl of about 0.25 M; and
the quantity of the viral particle inactivation is at least about 3 LRF (logarithmic reduction factor).

* * * * *

UNITED STATES PATENT AND TRADEMARK OFFICE
CERTIFICATE OF CORRECTION

| | |
|---|---|
| PATENT NO. | : 12,077,782 B2 |
| APPLICATION NO. | : 17/317602 |
| DATED | : September 3, 2024 |
| INVENTOR(S) | : Jena Daya, Valerie Ann Cusick and John Mattila |

It is certified that error appears in the above-identified patent and that said Letters Patent is hereby corrected as shown below:

On the Title Page

In item (56) the "PUBLICATIONS" section in the right-hand column at Line 13, delete "Polishand" and insert --Polish and--.

In item (56) the "PUBLICATIONS" section in the right-hand Column at Line 14, delete "HydrophobicInteraction" and insert --Hydrophobic Interaction--.

In the Claims

In Column 28, Line 11 of Claim 26, before "3.80," insert --pH--.

Signed and Sealed this
Fifth Day of November, 2024

Katherine Kelly Vidal
*Director of the United States Patent and Trademark Office*